United States Patent
Dobrinsky et al.

(10) Patent No.: US 10,869,943 B2
(45) Date of Patent: Dec. 22, 2020

(54) TREATMENT OF FLUID TRANSPORT CONDUIT WITH ULTRAVIOLET RADIATION

(71) Applicant: Sensor Electronic Technology, Inc., Columbia, SC (US)

(72) Inventors: Alexander Dobrinsky, Loudonville, NY (US); Michael Shur, Latham, NY (US)

(73) Assignee: Sensor Electronic Technology, Inc., Columbia, SC (US)

(*) Notice: Subject to any disclaimer, the term of this patent is extended or adjusted under 35 U.S.C. 154(b) by 233 days.

(21) Appl. No.: 15/471,584

(22) Filed: Mar. 28, 2017

(65) Prior Publication Data
US 2017/0281812 A1   Oct. 5, 2017

Related U.S. Application Data

(60) Provisional application No. 62/316,544, filed on Mar. 31, 2016.

(51) Int. Cl.
*A61L 2/10* (2006.01)
*A61L 2/08* (2006.01)
(Continued)

(52) U.S. Cl.
CPC .............. *A61L 2/10* (2013.01); *A61L 2/088* (2013.01); *B08B 7/0057* (2013.01); *B08B 9/0321* (2013.01); *A61L 2202/14* (2013.01)

(58) Field of Classification Search
CPC ......... A61C 1/0076; A61L 9/20; A61L 9/205; A61L 2/0047; A61L 2/10; A61L 2/088;
(Continued)

(56) References Cited

U.S. PATENT DOCUMENTS 5,874,740 A    2/1999  Ishiyama
6,919,019 B2 *  7/2005  Baca .................. C02F 1/325
                                          210/198.1
(Continued)

FOREIGN PATENT DOCUMENTS

JP    2011016074 A  *  1/2011

OTHER PUBLICATIONS

Machine Translation of Morito, JP-2011016074-A, Jan. 2011. (Year: 2011).*

(Continued)

*Primary Examiner* — David G Cormier
(74) *Attorney, Agent, or Firm* — LaBatt, LLC

(57) ABSTRACT

An approach for treating a fluid transport conduit with ultraviolet radiation is disclosed. A light guiding unit, operatively coupled to a set of ultraviolet radiation sources, encloses the fluid transport conduit. The light guiding unit directs ultraviolet radiation emitted from the ultraviolet radiation sources to ultraviolet transparent sections on an outer surface of the fluid transport conduit. The emitted ultraviolet radiation passes through the ultraviolet transparent sections, penetrates the fluid transport conduit and irradiates the internal walls. A control unit adjusts a set of operating parameters of the ultraviolet radiation sources as a function of the removal of contaminants from the internal walls of the fluid transport conduit.

20 Claims, 11 Drawing Sheets

(51) Int. Cl.
*B08B 7/00* (2006.01)
*B08B 9/032* (2006.01)

(58) Field of Classification Search
CPC ......... A61L 2/0076; A61L 2/24; B08B 7/005;
B08B 9/02; B08B 9/027; B08B 9/032;
B08B 9/0321; C02F 1/32; C02F 1/325;
C02F 2201/32; C02F 2201/322; C02F
2201/3222; C02F 2201/3224; C02F
2201/3226; C02F 2201/3227; C02F
2201/3228
See application file for complete search history.

(56) References Cited

U.S. PATENT DOCUMENTS

| | | | |
|---|---|---|---|
| 7,553,456 B2 | 6/2009 | Gaska et al. | |
| 7,634,996 B2 | 12/2009 | Gaska et al. | |
| 7,914,852 B2 | 3/2011 | Belz et al. | |
| 8,277,734 B2 | 10/2012 | Koudymov et al. | |
| 8,496,610 B2 | 7/2013 | Levenson et al. | |
| 8,980,178 B2 | 3/2015 | Gaska et al. | |
| 9,006,680 B2 | 4/2015 | Bettles et al. | |
| 9,061,082 B2 | 6/2015 | Gaska et al. | |
| 9,138,499 B2 | 9/2015 | Bettles et al. | |
| 9,179,703 B2 | 11/2015 | Shur et al. | |
| 9,572,903 B2 | 2/2017 | Dobrinsky et al. | |
| 9,603,960 B2 | 3/2017 | Dobrinsky et al. | |
| 9,687,577 B2 | 6/2017 | Dobrinsky et al. | |
| 9,718,706 B2 | 8/2017 | Smetona et al. | |
| 10,099,944 B2 | 10/2018 | Smetona et al. | |
| 2008/0164422 A1 | 7/2008 | Kim | |
| 2009/0250626 A1* | 10/2009 | Schlesser | A61L 2/0011 250/455.11 |
| 2013/0048545 A1 | 2/2013 | Shatalov et al. | |
| 2013/0126430 A1* | 5/2013 | Kenley | B01D 61/00 210/638 |
| 2014/0060094 A1 | 3/2014 | Shur et al. | |
| 2014/0060095 A1 | 3/2014 | Shur et al. | |
| 2014/0060096 A1 | 3/2014 | Shur et al. | |
| 2014/0060104 A1 | 3/2014 | Shur et al. | |
| 2014/0202962 A1 | 7/2014 | Bilenko et al. | |
| 2015/0008167 A1 | 1/2015 | Shturm et al. | |
| 2015/0069270 A1 | 3/2015 | Shur et al. | |
| 2015/0165079 A1 | 6/2015 | Shur et al. | |
| 2015/0217011 A1 | 8/2015 | Bettles et al. | |
| 2015/0297767 A1 | 10/2015 | Gaska et al. | |
| 2015/0336810 A1 | 11/2015 | Smetona et al. | |
| 2015/0344329 A1 | 12/2015 | Smetona et al. | |
| 2016/0000953 A1 | 1/2016 | Bettles et al. | |
| 2016/0058020 A1 | 3/2016 | Shur et al. | |
| 2016/0074548 A1 | 3/2016 | Dobrinsky et al. | |
| 2016/0077278 A1 | 3/2016 | Dobrinsky et al. | |
| 2016/0114186 A1 | 4/2016 | Dobrinsky et al. | |
| 2016/0128526 A1 | 5/2016 | Dobrinsky et al. | |
| 2016/0137528 A1* | 5/2016 | Wipprich | C02F 1/325 250/492.1 |
| 2016/0324996 A1 | 11/2016 | Bilenko et al. | |
| 2017/0057842 A1 | 3/2017 | Dobrinsky et al. | |
| 2017/0100494 A1 | 4/2017 | Dobrinsky et al. | |
| 2017/0100495 A1 | 4/2017 | Shur et al. | |
| 2017/0100496 A1 | 4/2017 | Shur et al. | |
| 2017/0157276 A1 | 6/2017 | Dobrinsky et al. | |
| 2017/0189711 A1 | 7/2017 | Shur et al. | |
| 2017/0197002 A1 | 7/2017 | Dobrinsky et al. | |
| 2017/0245527 A1 | 8/2017 | Dobrinsky et al. | |
| 2017/0245616 A1 | 8/2017 | Lakios et al. | |

OTHER PUBLICATIONS

International Application No. PCT/KR2017/003537, International Search Report and Written Opinion, dated Jun. 21, 2017, 15 pages.

* cited by examiner

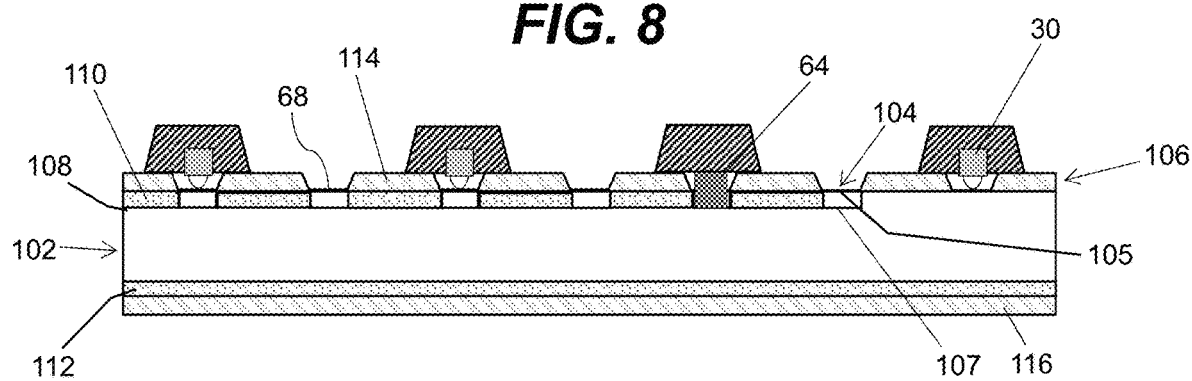
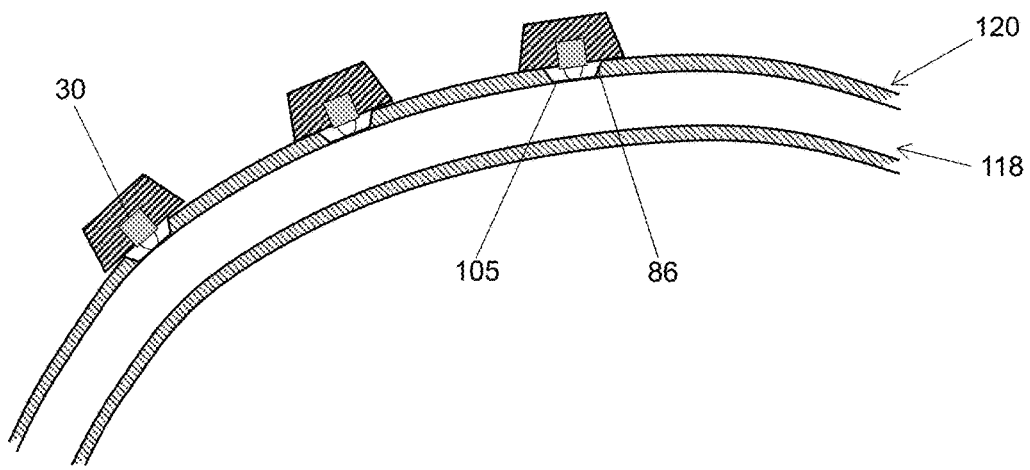

TREATMENT OF FLUID TRANSPORT CONDUIT WITH ULTRAVIOLET RADIATION

REFERENCE TO RELATED APPLICATIONS

The present patent application claims the benefit of U.S. Provisional Application No. 62/316,544, which was filed on 31 Mar. 2016, and which is hereby incorporated by reference.

TECHNICAL FIELD

The disclosure relates generally to conduits for transporting fluids, and more specifically, to a solution for treating (e.g., disinfecting, sterilizing, sanitizing, and/or the like) the internal walls of a conduit using ultraviolet radiation.

BACKGROUND ART

Coffee, tea and soda dispensing machines with feed lines for dispensing these fluids are examples of machines having conduits that transport fluids. The feed lines in these fluid dispensing machines generally suffer from the build-up of contaminants such as lime scale and bio-film. The build-up of lime scale and bio-film can become worrisome when the fluids dispensed in the feed lines have a bitter taste and/or an unpleasant odor. In addition, the accumulation of scale and bio-film can become a "home" for bacteria that can transfer to the dispensed fluid. Traditional approaches for removing lime scale and bio-film such as salt and chemical methods are not desirable as these modalities will affect the taste of the fluids dispensed from the machines. As a result, manual maintenance of the feed lines is necessary to remove the build-up of scale and the bio-film. Results from manual maintenance on the feed lines is inconsistent in terms of the effectiveness in removing the contaminants. Inconsistent removal of scale and bio-film causes the efficiency of the fluid dispensing machines to eventually suffer, which leads to higher energy and water costs. Furthermore, manual maintenance of the feed lines is costly in terms of labor, supplies, and machine downtime. With inconsistent results and high costs, manual maintenance of fluid dispensing machines to dislodge the build-up of scale and bio-film is not an ideal solution.

SUMMARY OF THE INVENTION

This Summary Of The Invention introduces a selection of certain concepts in a brief form that are further described below in the Detailed Description Of The Invention. It is not intended to exclusively identify key features or essential features of the claimed subject matter set forth in the Claims, nor is it intended as an aid in determining the scope of the claimed subject matter.

Aspects of the present invention are directed to ultraviolet cleaning or treating (e.g., disinfecting, sterilizing, sanitizing) of fluid transport conduits to remove contaminants that can accumulate on the internal walls of the conduits. Generally, the contaminants that can be removed with the ultraviolet cleaning or treating described herein include any physical, chemical, biological or radiological substance or matter that may form on the internal walls of the conduits. Examples of contaminants that can be removed include, but are not limited to, scale, bio-film, bacteria, viruses, germs, and the like. The various embodiments of the present invention are suitable for use with any conduit that is used to convey or distribute a fluid or liquid, where its internal walls are susceptible to the buildup of contaminants which present operational and/or health concerns over time if not removed. Examples of conduits can include, but are not limited to, piping, tubing, channel, ducts, passages, etc.

The various aspects of the present invention include a light guiding unit to direct ultraviolet radiation emitted from a set of ultraviolet radiation sources into the fluid transport conduit to irradiate internal walls of the conduit for removing contaminants therefrom. In one embodiment, the light guiding unit comprises a light guiding layer that encloses the fluid transport conduit. The light guiding layer can include a waveguide structure with an ultraviolet reflective layer, an ultraviolet extraction surface to diffusively scatter ultraviolet radiation, and an ultraviolet transparent layer formed between the ultraviolet reflective layer and the ultraviolet extraction surface. In one embodiment, the ultraviolet extraction surface can include a roughness layer having a roughness density that corresponds to a uniformity of the ultraviolet radiation exiting the ultraviolet extraction surface.

In operation, the light guiding layer can direct the ultraviolet radiation emitted from the set of ultraviolet radiation sources to ultraviolet transparent sections on an outer surface of the fluid transport conduit. The emitted ultraviolet radiation passes through the ultraviolet transparent sections, penetrates the fluid transport conduit and irradiates the internal walls. In one embodiment, the ultraviolet transparent sections on the outer surface of the fluid transport conduit can take the form of ultraviolet transparent windows. These windows can include materials such as, but not including, an ultraviolet transparent fluoropolymer, quartz, AAO, $SiO_2$, and sapphire. In one embodiment, the set of ultraviolet transparent windows can include an enclosure having a top wall, a bottom wall, a pair of side walls, a plurality of horizontal segments extending between the pair of side walls and a plurality of vertical segments extending between the top wall and the bottom wall. A set of voids can be formed between intersections of the plurality of horizontal segments and the plurality of vertical segments.

The ultraviolet transparent sections on the outer surface of the fluid transport conduit can also include a set of ultraviolet transparent domains. In one embodiment, each ultraviolet transparent domain can be located adjacent one of the ultraviolet transparent windows. In this manner, the ultraviolet transparent domains and the ultraviolet transparent windows are configured for ultraviolet transmission and light guiding of ultraviolet radiation emitted from the ultraviolet radiation sources to the internal walls of the fluid transport conduit. In one embodiment, the ultraviolet transparent sections can form rigid domains on the outer surface of the fluid transport conduit, while sections on the outer surface of the conduit without the ultraviolet transparent sections can form flexible domains.

In one embodiment, the outer surface of the light guiding layer can include a set of ports, wherein each port is configured to receive one of the ultraviolet radiation sources. A plurality of reflective elements can be configured for placement over the ports. In one embodiment, each port without an ultraviolet radiation source coupled thereto can have one of the plurality of reflective elements placed there over, while each port having an ultraviolet radiation source coupled thereto can have one of the reflective elements placed over both the ultraviolet radiation source and the port. Each port can be separated from an adjacent port by a distance L, wherein L is the distance that ultraviolet radiation emitted from one ultraviolet radiation source is partially attenuated. In one embodiment, L can be the distance that the ultraviolet radiation emitted from one ultraviolet radiation source has an intensity that is at least 30% of the intensity emitted at a location that the ultraviolet radiation source is placed. In another embodiment, L can be the distance between adjacent ultraviolet radiation sources, wherein the ultraviolet radiation propagating between the adjacent ultraviolet radiation sources has an intensity at half the distance L/2 that is equivalent to the intensity of the ultraviolet radiation emitted at a location of each of the adjacent ultraviolet radiation sources.

The set of ultraviolet radiation sources can be distributed over the fluid transport conduit in a variety of ways. For example, the ultraviolet radiation sources can be distributed over all of a surface area of the fluid transport conduit. In another embodiment, the ultraviolet radiation sources can cover only a limited portion of surface area of the fluid transport conduit. For example, the ultraviolet radiation sources can extend uniformly in an axial direction from a first end of the fluid transport conduit to an opposing second of end of the conduit.

In one embodiment, the fluid transport conduit can include a porous section extending from the outer surface of the conduit to its internal walls. In this embodiment, the light guiding layer can include a fluid intake port that is proximate the porous section of the fluid transport conduit. In this manner, a cleansing fluid from a cleansing fluid source can be delivered into the fluid intake port and through the porous section of the fluid transport conduit to clean the internal walls of the conduit.

In one embodiment, the fluid transport conduit can include a cleansing mixing unit configured to generate a mixing action in the fluid delivered in the fluid transport conduit. The mixing action can promote dislodgment of any contaminants that have accumulated on the internal walls of the fluid transport conduit. The cleansing mixing unit can operate in conjunction with the ultraviolet radiation sources to clean the walls of the fluid transport conduit.

Other modalities for cleaning the internal walls of the fluid transport conduit can be used in conjunction with light guiding layer and the ultraviolet radiation sources. For example, at least a portion of the internal walls of the fluid transport conduit can include an ultraviolet photo-catalyst for enhancing the effect of the ultraviolet radiation. In one embodiment, the ultraviolet photo-catalyst can incorporate a metal or semiconductor nanoparticles for achieving a plasmonic catalytic action. In another embodiment, the internal walls of the fluid transport conduit can include a non-biofouling material that can inhibit the formation and accumulation of certain contaminants. In one embodiment, a chemical de-scaler can operate in conjunction with the ultraviolet radiation sources to chemically remove contaminants from the internal walls of the fluid transport conduit.

A control unit can be deployed to adjust a set operating parameters for the ultraviolet radiation sources. The operating parameters can include a duration that the ultraviolet radiation sources emit ultraviolet radiation, a dosage of ultraviolet radiation delivered by the sources, a power setting for operating the sources. In one embodiment, the control unit can adjust these parameters as a function of the removal of contaminants from the internal walls of the fluid transport conduit.

One or more sensors can operate in conjunction with the control unit to control the ultraviolet radiation generated from the ultraviolet radiation sources to the internal walls of the fluid transport conduit. In one embodiment, an ultraviolet radiation sensor can be used to detect the intensity of the ultraviolet radiation propagating through the light guiding unit. In one embodiment, at least one sensor specific to one of the operating parameters can be used to monitor the corresponding parameter during the disinfecting of the internal walls of the fluid transport conduit. Other detection devices can be used in addition to, or in place of the sensors. For example, at least one visible camera can be used to determine an amount of contamination on the internal walls of the fluid transport conduit. The control unit can receive signals from the sensors representative of the measured parameter values, and control the disinfecting of the internal walls of the fluid transport conduit as a function of these measurements. In one embodiment, a power source unit can provide power to the ultraviolet radiation sources, the control unit and the sensors.

The various embodiments can be configured in one of a variety of implementations. For example, instead of solely having the ultraviolet radiation sources coupled to the light guiding layer, it is also possible to utilize a set of sources configured as an ultraviolet insert module that can be implemented for insertion within the interior of the fluid transport conduit. In this manner, the ultraviolet radiation sources in the insert module can be used to directly irradiate the internal walls of the conduit. In another embodiment, the ultraviolet radiation sources, the light guiding unit, the control unit and any other accompanying components such as sensors and a power source can form a disinfection module adapted for connection to the fluid transport conduit. In this manner, the disinfection module can be used as a cross-connection between two adjacent sections of the fluid transport conduit to clean these sections as well other section that are proximate thereto.

A first aspect of the invention provides a fluid transport conduit treatment system, comprising: a fluid transport conduit having a plurality of ultraviolet transparent windows distributed on an outer surface of the conduit; an outer conduit having a light guiding unit enclosing the fluid transport conduit; a plurality of ultraviolet radiation sources coupled to the light guiding unit, wherein each of the ultraviolet radiation sources is configured to emit ultraviolet radiation through at least one of the ultraviolet transparent windows that penetrates the fluid transport conduit and irradiates internal walls thereof; and a control unit to direct the plurality of ultraviolet radiation sources to deliver a predetermined dosage of ultraviolet radiation to the internal walls of the fluid transport conduit for a predetermined duration.

A second aspect of the invention provides a system, comprising: a fluid transport conduit; a plurality of ultraviolet radiation sources; a light guiding unit to direct ultraviolet radiation emitted from the plurality of ultraviolet radiation sources into the fluid transport conduit to irradiate internal walls of the fluid transport conduit for removing contaminants therefrom; a control unit to direct the plurality of ultraviolet radiation sources to emit a predetermined dosage of ultraviolet radiation to the internal walls of the fluid transport conduit via the light guiding unit for a predetermined duration; and a power source to provide power to the plurality of ultraviolet radiation sources and the control unit.

A third aspect of the invention provides a system for disinfecting internal walls of a fluid transport conduit, comprising: a light guiding layer enclosing the fluid transport conduit, wherein the light guiding layer comprises a waveguide structure having an ultraviolet reflective layer, an ultraviolet extraction surface to diffusively scatter ultraviolet radiation from the light guiding layer, and an ultraviolet transparent layer formed between the ultraviolet reflective layer and the ultraviolet extraction surface; a plurality of ultraviolet radiation sources operatively coupled to the light guiding layer to direct ultraviolet radiation to the internal walls of the fluid transport conduit, wherein the light guiding layer directs ultraviolet radiation emitted from the plurality of ultraviolet radiation sources to ultraviolet transparent sections on an outer surface of the fluid transport conduit, the emitted ultraviolet radiation passing through the ultraviolet transparent sections, penetrating the fluid transport conduit and irradiating the internal walls; and a control unit to adjust a plurality of operating parameters of the plurality of ultraviolet radiation sources as a function of removal of contaminants from the internal walls of the fluid transport conduit, wherein the plurality of operating parameters include a duration that the ultraviolet radiation sources emit ultraviolet radiation, a dosage of ultraviolet radiation delivered by the ultraviolet radiation sources, and a power setting for operating the ultraviolet radiation sources.

The illustrative aspects of the invention are designed to solve one or more of the problems herein described and/or one or more other problems not discussed.

BRIEF DESCRIPTION OF THE DRAWINGS

These and other features of the disclosure will be more readily understood from the following detailed description of the various aspects of the invention taken in conjunction with the accompanying drawings that depict various aspects of the invention.

FIG. 8 shows a schematic of a fluid transport conduit having ultraviolet transparent sections that include ultraviolet transparent windows and ultraviolet transparent domains proximate the windows according to embodiment.

FIG. 9 shows a schematic of a fluid transport conduit and a light guiding layer formed generally of a flexible material according to embodiment.

It is noted that the drawings may not be to scale. The drawings are intended to depict only typical aspects of the invention, and therefore should not be considered as limiting the scope of the invention. In the drawings, like numbering represents like elements between the drawings.

DETAILED DESCRIPTION OF THE INVENTION

Figure 1A:
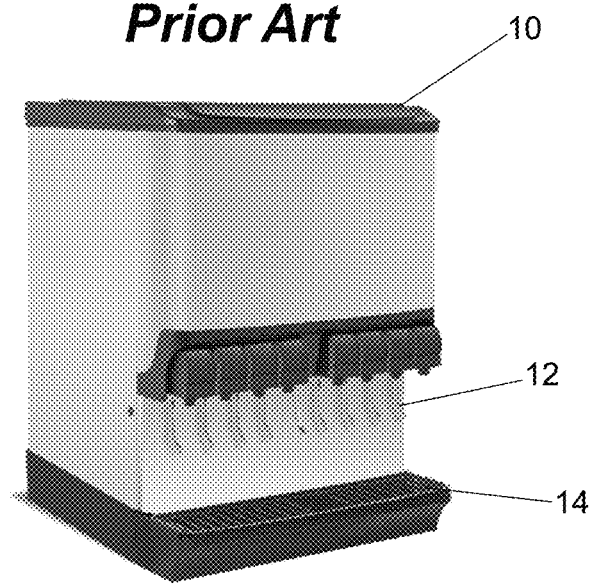
FIGS. 1A-1C schematically illustrate the build-up of contaminants that can plague fluid transport conduits used in fluid dispensing machines, such as for example, a soda dispensing machine.

As indicated above, aspects of the present invention are directed to ultraviolet cleaning or treating (e.g., disinfecting, sterilizing, sanitizing) of fluid transport conduits to remove contaminants that can accumulate on the internal walls of the conduit. Generally, the various embodiments are suitable for use with any conduit that can convey or distribute a fluid or liquid, and where its internal walls are susceptible to the buildup of contaminants which present operational and/or health concerns over time if not removed. Examples of fluid transport conduits can include, but are not limited to, piping, tubing, channels, ducts, passages, etc. The contaminants that can be removed with the ultraviolet cleaning or treating described herein can include any physical, chemical, biological or radiological substance or matter that may form on the internal walls of the conduits. Examples of contaminants that can be removed include, but are not limited to, scale, bio-film, bacteria, viruses, germs, and the like.

The various embodiments for cleaning the internal walls of a fluid transport conduit can include a number of components (some of which may be optional) described below in more detail that facilitate an ultraviolet cleaning treatment of a conduit. The modalities used with the various embodiments including its respective components can include any now known or later developed approaches that incorporate the concepts and configurations of the embodiments described herein.

As used herein, cleaning or treating a fluid transport conduit can entail dislodging or removing contaminants from the internal walls of the conduit, as well as sanitizing, disinfecting, and/or sterilizing the walls. Sanitizing generally means reducing a number of bacterial contaminants to a predetermined safe level. Disinfecting generally means destroying pathogenic and other types of microorganisms, while sterilizing can be more extensive in that it kills all microbial forms and/or include destroying the ability of the microbial forms to reproduce.

Ultraviolet radiation, which can be used interchangeably with ultraviolet light, means electromagnetic radiation having a wavelength ranging from approximately 10 nm to approximately 400 nm. Within this range, there is ultraviolet-A (UV-A) electromagnetic radiation having a wavelength ranging from approximately 315 nm to approximately 400 nm, ultraviolet-B (UV-B) electromagnetic radiation having a wavelength ranging from approximately 280 nm to approximately 315 nm, and ultraviolet-C (UV-C) electromagnetic radiation having a wavelength ranging from approximately 100 nm to approximately 280 nm.

Generally, ultraviolet radiation, and in particular, radiation with a wavelength ranging from 220 nm to 340 nm is sufficient to dislodge or remove contaminants from the internal walls of a fluid transport conduit. In one embodiment, radiation with a wavelength from 250 nm to 290 nm at a dose of about 20 to about 34 milliwatt-seconds/$cm^2$ is sufficient to deactivate approximately 99 percent of pathogens that can form on the internal walls of a fluid transport conduit. UV-B radiation and UV-C radiation is "germicidal," i.e., it deactivates the DNA of bacteria, viruses and other pathogens, and thus, can destroy their ability to multiply and cause disease. This effectively results in sterilization of the microorganisms. Specifically, UV-B radiation and UV-C radiation cause damage to the nucleic acid of microorganisms by forming covalent bonds between certain adjacent bases in the DNA. The formation of these bonds prevents the DNA from being "unzipped" for replication, and the organism is neither able to produce molecules essential for life process, nor is it able to reproduce. In fact, when an organism is unable to produce these essential molecules or is unable to replicate, it dies. Ultraviolet radiation with a wavelength of approximately between about 250 to about 290 nm provides the highest germicidal effectiveness and viral disinfection. While susceptibility to ultraviolet radiation varies, exposure to ultraviolet energy in the above range for about 20 to about 34 milliwatt-seconds/$cm^2$ is adequate to deactivate approximately 99 percent of the pathogens as stated above.

As used herein, a material/structure is considered to be "reflective" to ultraviolet light of a particular wavelength when the material/structure has an ultraviolet reflection coefficient of at least 30 percent for the ultraviolet light of the particular wavelength. A highly ultraviolet reflective material/structure has an ultraviolet reflection coefficient of at least 80 percent. Furthermore, a material/structure/layer is considered to be "transparent" to ultraviolet radiation of a particular wavelength when the material/structure/layer allows at least ten percent of radiation having a target wavelength, which is radiated at a normal incidence to an interface of the material/structure/layer to pass there through.

The description that follows may use other terminology herein for the purpose of describing particular embodiments only and is not intended to be limiting of the disclosure. For example, unless otherwise noted, the term "set" means one or more (i.e., at least one) and the phrase "any solution" means any now known or later developed solution. The singular forms "a," "an," and "the" include the plural forms as well, unless the context clearly indicates otherwise. It will be further understood that the terms "comprises", "comprising", "includes", "including", "has", "have", and "having" when used in this specification, specify the presence of stated features, integers, steps, operations, elements, and/or components, but do not preclude the presence or addition of one or more other features, integers, steps, operations, elements, components, and/or groups thereof.

Figure 1C:
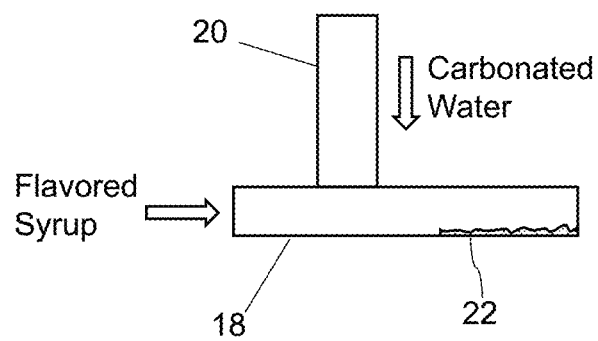
Figure 1B:
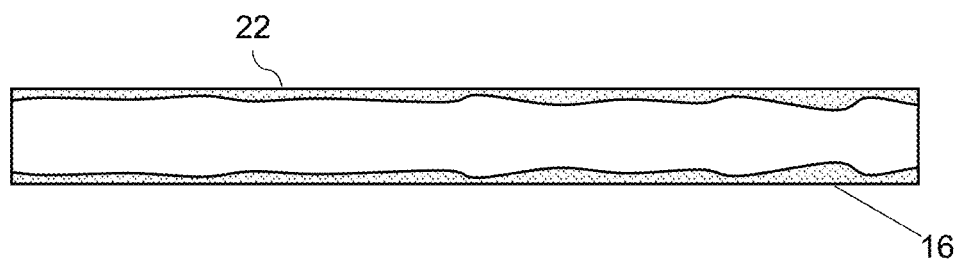

Turning to the drawings, FIGS. 1A-1C schematically illustrate a problem that a build-up of contaminants can have on fluid transport conduits used in fluid dispensing machines. The type of machine for this example as shown in FIG. 1A relates to a soda dispensing machine 10 having a set of dispensing tabs 12 that are each configured to serve a selected beverage into a cup upon a pressure applied to the tabs. Although the internal components of the fluid dispensing machine 10 are not illustrated in FIG. 1A, it is understood that it can include a pressure-sealed water container, a carbon dioxide ($CO_2$) cylinder, and containers of flavored syrups each corresponding to one of the beverages that can be served to a user upon pressing the applicable dispensing tab 12. Upon selection of one of the dispensing tabs 12, carbonated water is released and a specified amount of flavored syrup is supplied to the carbonated water. Although the amount of flavored syrup that is supplied to the carbonated water can vary, it is usually a greater amount than the water, such as for example, a 5:1 to ratio of flavored syrup to carbonated water. A feed line (e.g., piping or tubing) corresponding to the selected beverage supplies the fluid to the dispensing tab 12 where a customer typically has a cup awaiting to receive the dispensed beverage. An excess beverage tray 14 can receive any fluid that overflows the cup or an amount that the user does not desire to consume.

The feed lines that dispense these fluids suffer from the build-up of contaminants such as lime scale and bio-film. As shown in FIGS. 1B-1C, the contaminants that can accumulate on a feed line 16, include the lines that provide the flavored syrup 18 and the carbonated water 20. In particular, the contaminants can accumulate on the internal walls of the feed lines in the form of plaque 22 deposits. The plaque 22 can accumulate anywhere on the internal walls of the feed lines, however, the deposits usually form on sections of the feed lines that carry a combination of the flavored syrup and the carbonated water as depicted in FIG. 1C. The build-up of contaminants on the internal walls of the feed lines can lead to fluids being dispensed with a bitter taste and/or an unpleasant odor. In addition, the accumulation of the contaminants can become a "home" for bacteria that can transfer to the beverage. The environment for bacteria proliferation becomes more prevalent as a result of the mixing of the carbonated water and the flavored syrup which usually contains large amounts of sugar. Current approaches to cleaning the feed lines which includes manually cleaning the lines is not an ideal solution due its inconsistent results, large amounts of machine downtime, and high costs.

Embodiments of the present invention are designed to provide solutions that reduce or eliminate contamination from the feed lines. It is understood that the build-up of contaminants on the internal walls of feed lines can plague a number of fluid dispensing machines that have fluid transport conduits used to supply a fluid. The embodiments of the present invention are suitable for use with any fluid dispensing machines that have fluid transport conduits that are subject to the buildup of contaminants such as plaque, scale, biofilm and the like, which make maintenance and downtime of the machines a frequent event.

Figure 2A:
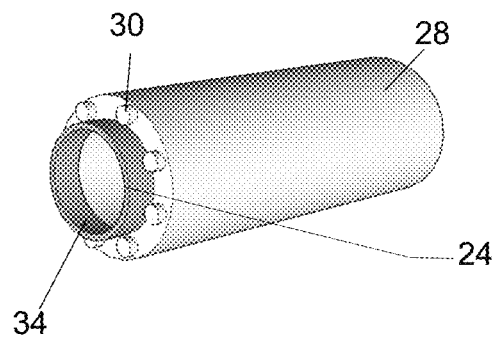
FIG. 2A-2B show schematics of a fluid transport conduit having ultraviolet transparent sections enclosed by a light guiding unit coupled with a set of ultraviolet radiation sources according to embodiment.
Figure 2B:
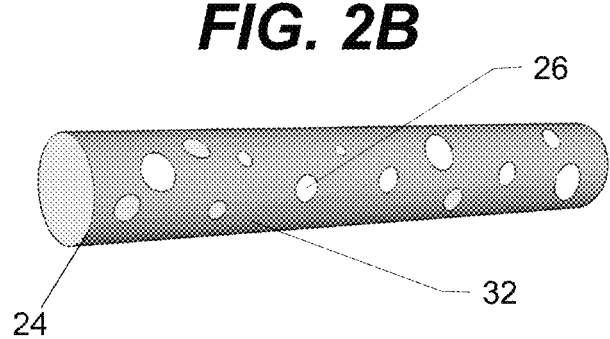

According to one embodiment of the present invention, FIGS. 2A-2B show a schematic of a fluid transport conduit 24 having ultraviolet transparent sections 26 enclosed by a light guiding unit 28 coupled to a set of ultraviolet radiation sources 30. In one embodiment, the ultraviolet transparent sections 26 can include a plurality of ultraviolet transparent windows distributed on an outer surface 32 of the conduit

24. The light guiding unit 28, which in this embodiment surrounds the fluid transport conduit 24 can include the set of ultraviolet radiation sources 30. Each of the ultraviolet radiation sources 30 is configured to emit ultraviolet radiation through at least one of the ultraviolet transparent windows. The ultraviolet radiation penetrates the fluid transport conduit 24 and irradiates internal walls 34 of the conduit.

Although not shown in these figures, a control unit can be used to direct the set of ultraviolet radiation sources 30 to deliver a predetermined dosage of ultraviolet radiation to the internal walls 34 of the fluid transport conduit 24 for a predetermined duration. In this manner, the ultraviolet radiation sources 30 can deliver a sufficient amount of ultraviolet radiation to the internal walls 34 of the fluid transport conduit 24 that dislodges or removes any contaminants that have accumulated on the walls. This treatment of the internal walls 34 of the fluid transport conduit 24 with ultraviolet radiation minimizes the buildup of germs and bacteria on the walls that have the potential to mix with the fluid supplied in the conduit and be consumed, which is not desirable from a health safety point of view.

The set of ultraviolet transparent windows distributed on the outer surface 32 of the conduit 24 enable the ultraviolet radiation emitted from the ultraviolet radiation sources 30 to penetrate the fluid transport conduit 24 and irradiate the internal walls 34 of the conduit, enabling the eradication and suppression of a number of organisms that can threaten the health of someone who drinks a beverage that contains contaminants residing within the conduit. The ultraviolet transparent windows can include, but are not limited to, an ultraviolet transparent fluoropolymer, quartz, AAO, $SiO_2$, and sapphire. Examples of an ultraviolet transparent fluoropolymer material can include, but are not limited to, fluorinated ethylene propylene co-polymer (EFEP), fluorinated ethylene propylene (FEP), polytetrafluoroethylene (PTFE), ethylene chlorotrifluoroethylene (ECTFE), polychlorotrifluoroethylene (PCTFE), perfluoroalkoxy (PFA), polyvinylidene fluoride (PVDF), ethylene tetrafluoroethylene (ETFE), tetrafluoroethylene hexafluoropropylene vinylidene fluoride co-polymer (THV), low density polyethylene (LDPE), perfluoro methyl alkoxy (MFA), Teflon®, and/or the like. While primarily described in conjunction with fluoropolymers, it is understood that other comparable materials can be utilized such as polylactide (PLA), fused silica, sapphire, THE, ultraviolet transparent glass, ultraviolet transparent crystal, and/or the like. Other transparent materials can include, but are not limited to, $SiO_2$, $TiO_2$, $Al_2O_3$, $CaF_2$, $MgF_2$.

Figure 3:
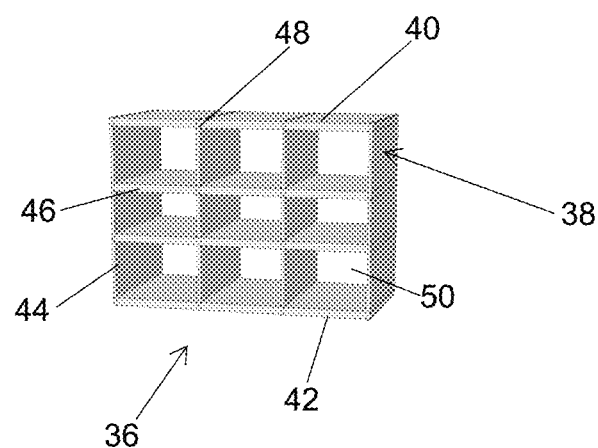
FIG. 3 shows a schematic of a structure of an ultraviolet transparent window that can be utilized with the fluid transport conduit according to an embodiment.

The set of ultraviolet transparent windows can be configured in one of a number of forms to allow the passage of ultraviolet radiation emitted from the ultraviolet radiation sources 30. For example, FIG. 3 shows a schematic of a structure of an ultraviolet transparent window 36 that can be utilized with a fluid transport conduit. In one embodiment, the window 36 can include an enclosure 38 having a set of thin layers engineered to provide a mechanically solid structure with a set of voids to allow for improved transparency. As shown in FIG. 3, the enclosure 38 can have a top wall 40, a bottom wall 42, a pair of side walls 44, a set of horizontal segments 46 extending between the pair of side walls and a set of vertical segments 48 extending between the top wall and the bottom wall. With this configuration, a set of voids 50 can be formed between intersections of the horizontal segments 46 and the vertical segments 48.

Referring back to FIGS. 2A-2B, each of the ultraviolet radiation sources 30 can be located within the light guiding unit 28. For example, the ultraviolet radiation sources 30 can adhere to an inner surface of the light guiding unit 28 or the sources can be integrated within the unit such that the emitting faces of the sources are oriented to emit ultraviolet light towards the ultraviolet transparent sections 26 to effectuate a cleaning treatment of the internal walls 34 of the fluid transport conduit 24.

The set of ultraviolet radiation sources 30 can comprise any combination of one or more ultraviolet radiation emitters. Examples of ultraviolet radiation emitters can include, but are not limited to, high intensity ultraviolet lamps (e.g., high intensity mercury lamps), discharge lamps, ultraviolet LEDs, super luminescent LEDs, laser diodes, and/or the like. In one embodiment, the set of ultraviolet radiation sources 30 can include a set of LEDs manufactured with one or more layers of materials selected from the group-III nitride material system (e.g., $Al_xIn_yGa_{1-X-Y}N$, where $0\leq x$, $y \leq 1$, and $x+y \leq 1$ and/or alloys thereof). Additionally, the set of ultraviolet radiation sources 30 can comprise one or more additional components (e.g., a wave guiding structure, a component for relocating and/or redirecting ultraviolet radiation emitter(s), etc.) to direct and/or deliver the emitted radiation to a particular location/area, in a particular direction, in a particular pattern, and/or the like. Illustrative wave guiding structures include, but are not limited to, a waveguide, a plurality of ultraviolet fibers, each of which terminates at an opening, a diffuser, a light guiding layer, a light diffusing layer, and/or the like.

It is understood that the number of ultraviolet radiation sources 30 illustrated in FIG. 2A and the other embodiments depicted in the remaining figures is only illustrative. Those skilled in the art will appreciate that any number of ultraviolet radiation sources may be located within the light guiding unit 28.

In order to effectuate a cleaning treatment of the internal walls 34 of the fluid transport conduit 24, the ultraviolet radiation sources 30 can be configured to be operated at a number of wavelengths. For example, in one embodiment, the ultraviolet radiation sources 30 can be configured to operate at a wavelength that ranges from about 250 nm to about 290 nm. In another embodiment, the ultraviolet radiation sources 30 can be configured to operate concurrently at multiple wavelengths. For example, at least one ultraviolet radiation source 30 can operate at a first wavelength with a peak wavelength of 280 nm, while at least one other source can operate a second wavelength at peak wavelength of 250 nm, with each having a wavelength range of about 20 nm. Emission of ultraviolet light within this wavelength range for a predetermined time period, with a dosage ranging from about 20 to about 34 milliwatt-seconds/$cm^2$ is sufficient to effectively clean the internal walls 34 of the fluid transport conduit 24 from a germicidal effectiveness point of view.

It is understood that the ultraviolet radiation sources 30 can be configured to function in other coordinated manners. For example, the ultraviolet radiation sources 30 can operate at the same wavelengths and intensities for the same duration, or the sources can operate at different wavelengths and intensities for varying durations. In one embodiment, a first set of ultraviolet radiation sources 30 can operate at a target wavelength and intensity that is designed for the disinfection of bacteria and/or viruses, while a second set of ultraviolet radiation sources 30 can operate at a different target wavelength and intensity that is designed for removal or dislodgement of contaminants from the internal walls 34 of the fluid transport conduit 24.

The control unit, which is explained below in more detail with regard to FIGS. 15-16, can be used to initiate a cleaning treatment of the internal walls 34 of the fluid transport conduit 24. The control unit can specify a plurality of operating parameters for the cleaning treatment of the internal walls 34 of the fluid transport conduit 24. The plurality of operating parameters can include, but are not limited to, a cleaning treatment time or duration that the ultraviolet radiation sources 30 emit the ultraviolet radiation, a dosage of ultraviolet radiation delivered by the ultraviolet radiation sources 30, a power setting for operating the ultraviolet radiation sources, and a maximum operating temperature for the ultraviolet cleaning treatment. It is understood that these operating parameters are illustrative of some of the parameters that can be set by the control unit and is not meant to be limiting as other parameters exist which may be specified such as a wavelength of the ultraviolet light used for disinfection, and/or the like.

Other components in addition to the control unit can be used to effectuate a cleaning treatment of the internal walls 34 of the fluid transport conduit 24. For example, at least one sensor can be configured to monitor one of the operating parameters during the cleaning treatment and to provide signals thereof to the control unit. The control unit can control the operation of the cleaning treatment as a function of the signals received from the sensors and adjust the parameters in a manner that corresponds to the removal of contaminants from the internal walls 34 of the fluid transport conduit 24. Examples of sensors that can be used include, but are not limited to, bacterial fluorescence sensors, visible light sensors, temperature sensors, pressure sensors, chemical sensors, radiation sensors (e.g., an ultraviolet dose counter or meter), a visible camera, etc.

In one embodiment, a bacterial fluorescence sensor can detect the amount or regions where there is a presence of bacteria, germs, viruses, and/or the like, which is present on the internal walls 34 of the fluid transport conduit 24. For example, the bacterial fluorescence sensor can generate signals representative of the condition of the walls with respect to the amount of bacteria, germs, viruses, and the like, and send those signals to the control unit. The control unit can in turn determine whether a cleaning treatment is necessary as a function of the feedback signals provided by the bacterial fluorescence sensor using any solution and direct the ultraviolet radiation sources 30 to direct radiation to the applicable area with appropriate intensity. In one embodiment, the control unit can activate the operation of the ultraviolet radiation sources 30 in response to determining that the internal walls 34 of the fluid transport conduit 24 have an amount of bacteria, germs, viruses, and/or the like, which exceeds a predetermined threshold, and thus, requires a cleaning treatment. Activating the operation of the ultraviolet radiation sources 30 by the control unit can include specifying the aforementioned operating parameters. In addition, the control unit can use the signals from the sensors to adjust a current treatment cycle of the fluid transport conduit 24.

In other embodiments, the control unit can include a timer with switches and/or the like, to manage the duration that the ultraviolet radiation sources 30 are on for a particular cleaning treatment, and ensure that radiation is applied to the internal walls 34 of the fluid transport conduit 24 for that duration (e.g., a dosage timer). In one embodiment, the control unit operating in conjunction with the timer can manage the amount of time that the ultraviolet radiation sources 30 radiate in the UV-C range versus the UV-B range. The duration and frequency treatment that the ultraviolet radiation sources 30 are utilized can depend on detected condition signals provided to the control unit by any of the sensors.

During operation of a cleaning treatment, the control unit can be used to control at least one of a plurality of predetermined ultraviolet radiation characteristics associated with the ultraviolet radiation emitted from the ultraviolet radiation sources 30. The predetermined ultraviolet radiation characteristics that can be controlled by the control unit can include wavelengths, intensities, and durations and/or the like. In one embodiment, the control unit can control the wavelength of ultraviolet radiation and intensity spatially over the internal walls 34 of the fluid transport conduit 24. As an example, the control unit can control the ultraviolet radiation sources 30 to operate at a target wavelength and intensity for a duration that is designed for the disinfection of bacteria and/or viruses on the internal walls 34 of the fluid transport conduit 24.

In an embodiment, the control unit can determine the target intensity of the radiation based on an amount of time since a previous cleaning has been performed. For example, the control unit can implement an algorithm in which a minimum ultraviolet intensity is utilized when a previous cleaning was performed within a certain period of time, and the intensity is increased to a maximum intensity, which is utilized when the previous cleaning was performed over a maximum period of time. The intensity range can be determined based on attributes of the ultraviolet radiation sources 30. The target intensity can be incremented in steps or continuously over the range of times corresponding to the varying intensities. The range of times can be determined based on, for example, feedback data acquired regarding a severity of contamination typical for a period of time. In an embodiment, the control unit can generate a warning signal for presentation to a user when the time period since a previous cleaning has exceeded a maximum recommended time (e.g., time period corresponding to the maximum ultraviolet radiation). The warning signal can be generated using any type of output device including, for example, a vibration device, a visible light (e.g., flashing), an auditory signal generated by a speaker, and/or the like.

In addition, during the operation of the cleaning treatment, the control unit can be used to turn on or off the ultraviolet radiation sources 30 dependent upon the detected conditions provided by any sensors. Also, the control unit can be used to adjust one or more of the ultraviolet radiation characteristics based on the conditions detected by the sensors. For example, the control unit can use the signals from a bacterial fluorescence sensor that are representative of the amount of bacteria, germs, viruses, and/or the like, present on the internal walls 34 of the fluid transport conduit 24 to adjust the intensity, the wavelength, the duration and/or the pattern of the ultraviolet radiation emitted from any of the ultraviolet radiation sources 30. In another embodiment, the control unit can be configured to interrupt the operation of the ultraviolet radiation sources 30 in response to receiving temperature signals from a temperature sensor and determining that the temperature of the cleaning treatment has exceeded the maximum temperature. The control unit can resume the cleaning treatment after a predetermined cooling time has elapsed.

In one embodiment, the control unit can also include a wireless transmitter and receiver that is configured to communicate with a remote location via Wi-Fi, BLUETOOTH, and/or the like. As used herein, a remote location is a location that is apart from a fluid dispensing machine having the fluid transport conduit 24. For example, a remote computer can be used to transmit operational instructions to the wireless transmitter and receiver. The operational instructions can be used to program functions performed and managed by the control unit. In another embodiment, the wireless transmitter and receiver can transmit cleaning treatment results, data from the sensors to the remote computer, to facilitate maintenance and diagnostic operations on the cleaning of the internal walls 34 of the fluid transport conduit 24.

In one embodiment, the control unit can include an input component and an output component to allow a user to interact with the cleaning of the fluid dispensing machine including its fluid transport conduits and to receive information regarding the treatment. In one embodiment, the input component can permit a user to adjust at least one of the aforementioned plurality of operating parameters. This can include making adjustments during the cleaning treatment operation and/or prior to initiating a treatment. In one embodiment, the input component can include a set of buttons and/or a touch screen to enable a user to specify various input selections regarding the operating parameters as well as the cleaning treatment. In one embodiment, the output component can include a visual display for providing status information on the cleaning treatment (e.g., time remaining, the presence of bacteria, viruses, germs or the like), an indication that a cleaning treatment is recommended, an indication that the device has been sterilized, disinfected, sanitized, an indication that the device has been disinfected, sanitized, an indication after its last use, a simple visual indicator that displays whether a cleaning treatment is underway (e.g., an illuminated light), or if the treatment is over (e.g., absence of an illuminated light).

Another component not illustrated in FIGS. 2A-2B that can be used in the cleaning of the fluid transport conduit 24 is a power source that is configured to power each of the ultraviolet radiation sources 30, the control unit and the sensors. In one embodiment, the power source can take the form of one or more batteries, a vibration power generator that can generate power based on magnetic inducted oscillations or stresses developed on a piezoelectric crystal. In another embodiment, the power source can include a super capacitor that is rechargeable. Other power components that are suitable for use as the power source can include a mechanical energy to electrical energy converter such as a piezoelectric crystal, and a rechargeable device.

Figure 14A:
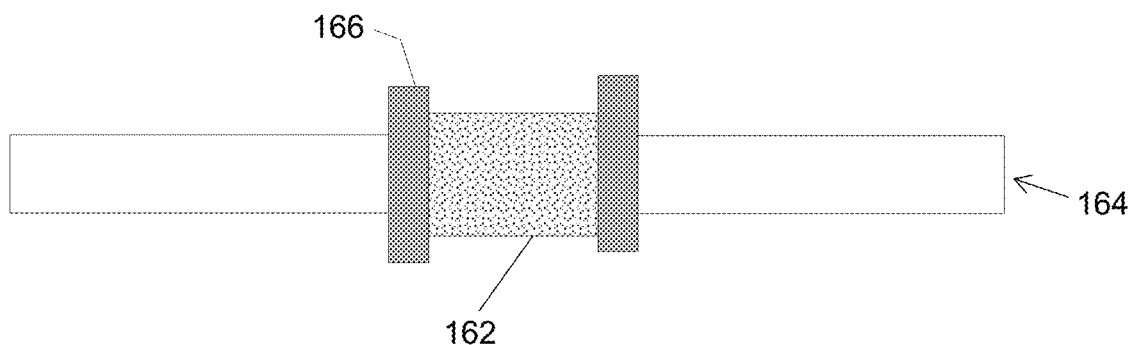
FIGS. 14A-14B show schematics of disinfection modules having ultraviolet radiation sources, a light guiding unit, and a control unit that can be adapted for connection to a fluid transport conduit to clean its internal walls according to an embodiment.
Figure 14B:
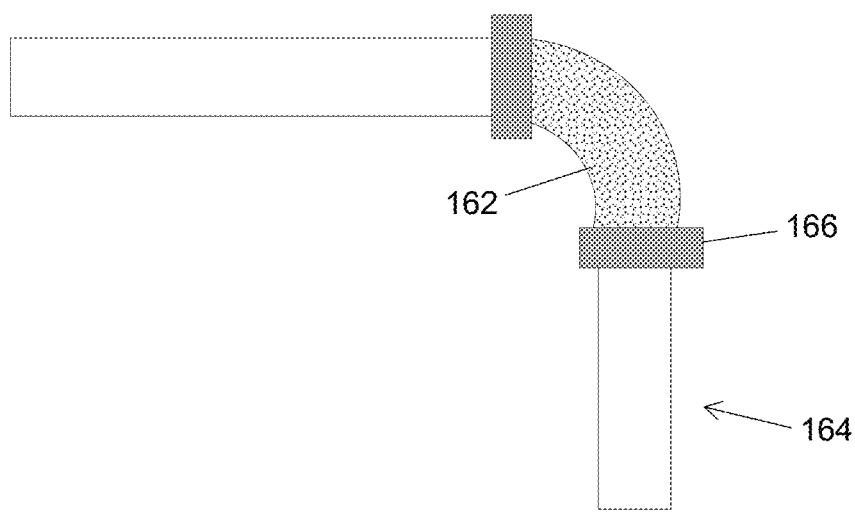
Figure 15:
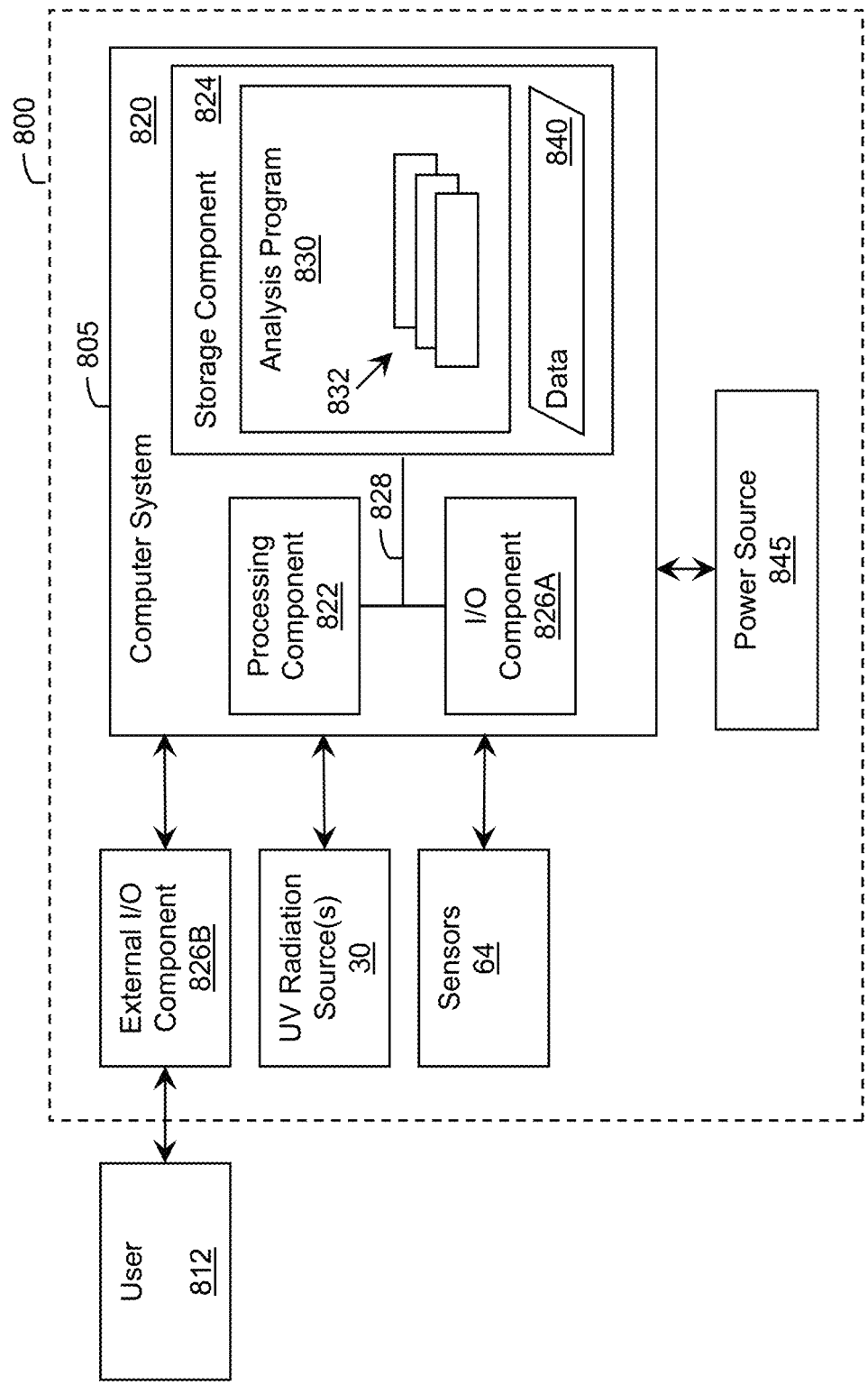
FIG. 15 shows a schematic of an ultraviolet cleaning unit that can be implemented with any of the embodiments depicted in FIGS. 2-14 according to an embodiment.
Figure 16:
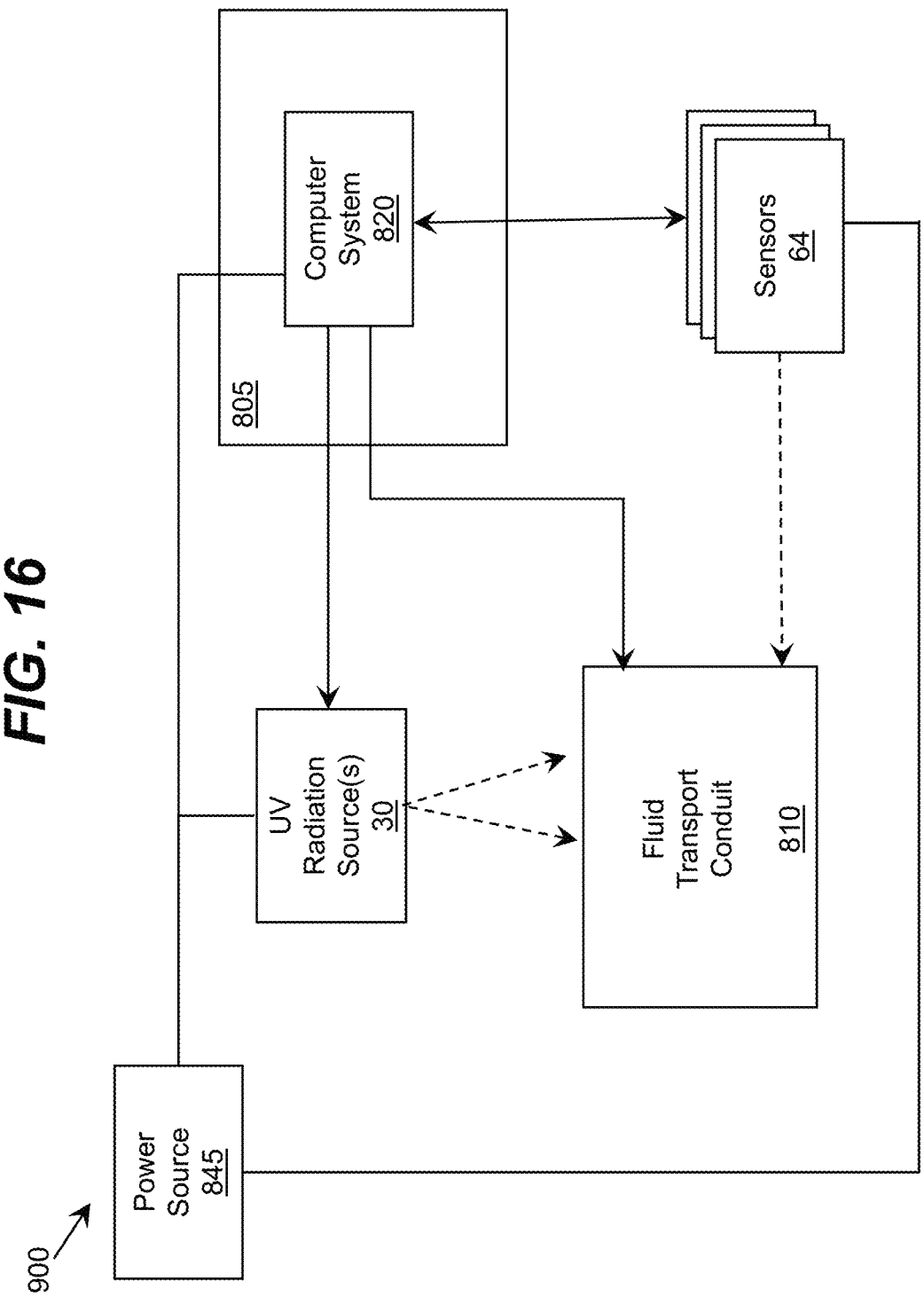
FIG. 16 shows a schematic of an illustrative environment in which the ultraviolet cleaning unit depicted in FIG. 15 can be used to facilitate a cleaning treatment of the internal walls of a fluid transport conduit according to an embodiment.

Further details of these components are illustrated in FIGS. 15-16 and discussed further with regard to these figures. These components are suitable for use as a system for facilitating an ultraviolet cleaning treatment of the fluid transport conduit 24 depicted in FIGS. 2A-2B, as well as with the other embodiments depicted in FIGS. 3-14. It is understood that the functions of these components can vary and will depend on the fluid dispensing machine and the type of fluid transport conduits used in such machines. Thus, the functions described are only illustrative of examples of particular functions and operations to be performed, and are not meant to be limiting to the embodiment of FIGS. 2A-2B, as well as with the embodiments pertaining to FIGS. 3-14.

Figure 4:
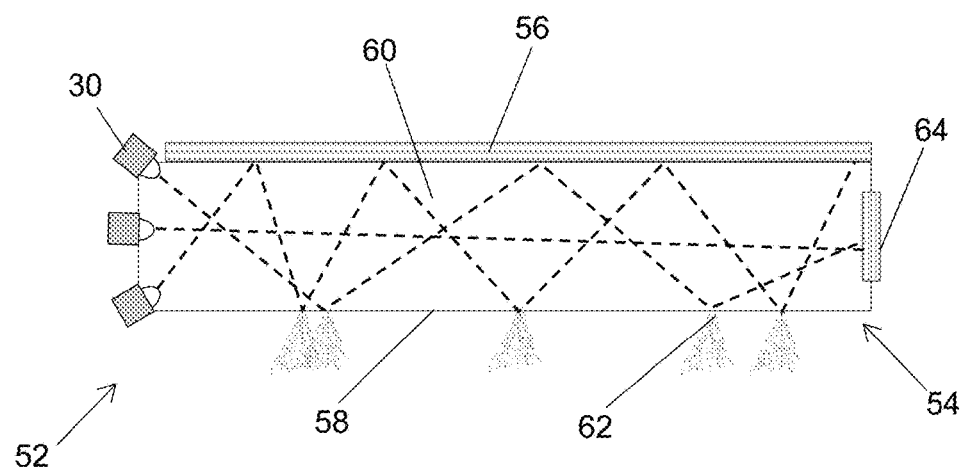
FIG. 4 shows a schematic of a light guiding layer that can be used with the light guiding unit according to an embodiment.

FIG. 4 shows a schematic of a light guiding layer 52 that can be used as a light guiding unit according to an embodiment. In this embodiment, the light guiding layer 52 can include a waveguide structure 54 that guides the ultraviolet radiation emitted from the ultraviolet radiation sources 30 coupled to the light guiding layer 52. As shown in FIG. 4, the ultraviolet radiation sources 30 can be coupled to the light guiding layer 52 at one end. For example, in an embodiment in which the light guiding layer 52 and the fluid transport conduit that it encloses, take the form of a cylinder, the ultraviolet radiation sources 30 can be disposed about the entire surface area of the circumference of that one end. In this manner, the waveguide structure 54 of the light guiding layer 52 can guide the ultraviolet radiation from the ultraviolet radiation sources 30 to the opposing end of the cylinder shape of the guiding layer.

In one embodiment, as shown in FIG. 4, the waveguide structure 54 can include an ultraviolet reflective layer 56, an ultraviolet extraction surface 58 to diffusively scatter a fraction of ultraviolet radiation from the light guiding layer 52 into the interior of a fluid transport conduit (not illustrated). An ultraviolet transparent layer 60 can be formed between the ultraviolet reflective layer 56 and the ultraviolet extraction surface 58.

The ultraviolet reflective layer 56 facilitates the recycling or recirculation of the ultraviolet radiation emitted from the ultraviolet radiation sources 30. In one embodiment, the ultraviolet reflective layer 56 can be disposed above the ultraviolet extraction surface 58, with the ultraviolet radiation sources 30 positioned in between. The emitting faces of the sources 30 can be oriented at different angles in order to deliver the ultraviolet radiation along the waveguide structure 54. As shown in FIG. 4, the rays of light from the ultraviolet radiation sources 30 reflect off the ultraviolet reflective layer 56 and the ultraviolet extraction surface 58 while propagating along the ultraviolet transparent layer 60 toward the other end of the waveguide structure 54. In one embodiment, the ultraviolet reflective layer 56 can have a reflection coefficient of at least 50% in order to enable recycling of the ultraviolet radiation generation from the ultraviolet radiation sources 30. In one embodiment, the ultraviolet reflective layer 56 can include polished aluminum, PTFE, GORE®, Teflon®, ETFE or combinations thereof.

In another embodiment, the ultraviolet reflective layer 56 can include a diffusive ultraviolet reflective layer. The diffusive ultraviolet reflective layer can include a coating or thin film of a fluoropolymer. Examples of a fluoropolymer that are suitable as an ultraviolet reflective material that enables diffusive reflectivity can include, but are not limited to, expanding polytetrafluoroethylene (ePTFE) membrane (e.g., GORE® DRP® Diffuse Reflector Material), polytetrafluoroethylene (PTFE), and/or the like.

The ultraviolet transparent layer 60 can have a transparency that is sufficient for propagation of light to travel from the end of the waveguide structure in which the ultraviolet radiation sources 30 emit the radiation to the opposite end of the structure. In one embodiment, the ultraviolet transparent layer 60 can have a transparency of about 25% to 100%. In one embodiment, the ultraviolet transparent layer 60 can include a transparent material such as for example, fused ultraviolet Si, $CaF_2$, $MgF_2$, crystal quartz, and fluoropolymers.

As shown in FIG. 4, the ultraviolet extraction surface 58 can include light exiting regions 62 where the light from the ultraviolet radiation sources 30 exits the wave guiding structure 54 diffusively towards the ultraviolet transparent sections of the fluid transport conduit. The diffusive scattering of light from the light exiting regions 62 can be achieved by applying a roughness layer or component to the ultraviolet extraction surface 58. As used herein, a roughness layer or component includes any material such as one of the aforementioned ultraviolet transparent materials, or a composite material, such as alumina with semiconductor or metallic nanoparticles incorporated therein. In one embodiment, the roughness layer can have a roughness density that corresponds to a uniformity of the ultraviolet radiation exiting the ultraviolet extraction surface 58. For example, the roughness density throughout the waveguide structure 54 can be largely uniform along the ultraviolet extraction surface 58. In one embodiment, the roughness density can increase as a distance from a particular ultraviolet radiation source 30 or a collection of sources.

In one embodiment, the waveguide structure 54 can include at least one sensor 64 located at an end opposite the set of ultraviolet radiation sources 30. For example, in one embodiment, the sensor 64 can include an ultraviolet radiation sensor to detect the intensity of the ultraviolet radiation propagating through the waveguide structure 54. In addition to sensing the intensity of the ultraviolet radiation, the ultraviolet radiation sensor 64 can serve as a reflecting surface that complements the ultraviolet reflective layer 56. It is understood that with the sensor 64 located at an end of the waveguide structure 54 that is opposite the set of ultraviolet radiation sources 30, the transparency of the ultraviolet transparent layer 60 can be selected to have sufficient propagation of light from the sources 30 to the other end so that the sensor can determine the intensity of the ultraviolet light.

It is understood that although the waveguide structure 54 depicted in FIG. 4 has one sensor 64, more than one sensor can be deployed. Additional sensors can be located at that one end of the waveguide structure 54 and/or along the interior walls of the waveguide. The additional sensor(s) can include other ultraviolet radiation sensors and/or any of the aforementioned sensors such as for example, bacterial fluorescence sensors, visible light sensors, temperature sensors, pressure sensors, chemical sensors, radiation sensors (e.g., an ultraviolet dose counter or meter), a visible camera, etc.

Figure 5:
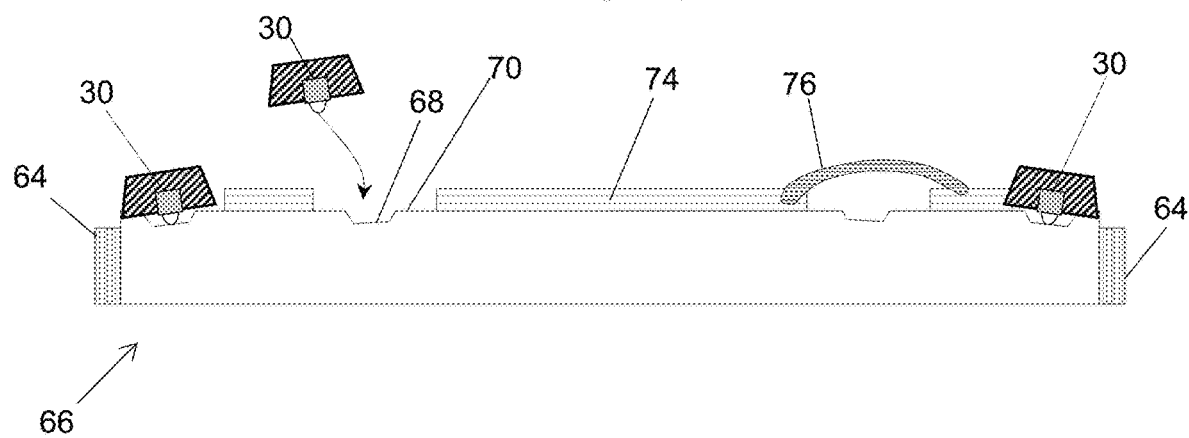
FIG. 5 shows a schematic of a light guiding layer having ports for coupling with ultraviolet radiation sources, reflective elements formed over some of the ports, and at least one sensor according to an embodiment.

FIG. 5 shows a schematic of a light guiding layer 66 according to another embodiment. In this embodiment, the light guiding layer 66 can include a set of ports 68 for coupling with a set of ultraviolet radiation sources 30. In one embodiment, the ports 68 can be formed on a top surface 70 of the light guiding layer 66. As shown in FIG. 5, the ports 68 can be located between a reflective layer 74 disposed on the top surface 70. In one embodiment, the reflective layer 74 can include, but is not limited to, aluminum. It is understood that the number and location of the ports 68 can vary and that the configuration of these ports as shown in FIG. 5 is not meant to be limiting.

The ultraviolet radiation sources 30 can be attached to the light guiding layer 66 through the ports 68 by a number approaches. For example, quartz or alumina optical elements can be used to couple the ultraviolet radiation sources 30 to the ports 68. In one embodiment, the number of ultraviolet radiation sources 30 that are attached to the ports 68 can match the target density of the ultraviolet radiation within the light guiding layer 66.

In one embodiment, a set of reflective elements 76 that are reflective to ultraviolet radiation can be placed over the ports 68 and the ultraviolet radiation sources 30. The reflective elements 76 can be placed over ports 68 that are not coupled with an ultraviolet radiation source 30. As shown in FIG. 5, the reflective element 76 can extend between sections of the reflective layer 74, spanning over all of the port as well as sections on the top surface 70 that do not have any of the reflective layer 74. The reflective elements 76 can also be placed over any of the ultraviolet radiation sources 30 coupled to a port 68. For example, a reflective element 76, that can include aluminum layers, can be placed on adjacent sections of the reflective layer 74 that are separated by the port 68. In this manner, the reflective element 76 can form a bridge extending over the ultraviolet radiation source 30 and the port 68.

The light guiding layer 66 can also include at least one sensor 64 to monitor any one of the aforementioned operating parameters that a control unit can monitor during the disinfecting of the internal walls of a fluid transport conduit. In the embodiment depicted in FIG. 5, the light guiding layer 66 can have two sensors 64 each located at an opposing end of the layer. In this example, the sensors 64 can include photodiodes, opto field-effect transistors (FETs), or fluorescent strips that detect radiation intensity as a function of time, temperature, and humidity. It is understood that any additional sensors can be located along the interior walls of the light guiding layer 66.

In one embodiment, a power source (not depicted) that powers the ultraviolet radiation sources 30, the sensors 64 and a control unit (not depicted) could be charged by fluid motion of the fluid that is transported in a fluid transport conduit. In another embodiment, a difference in temperature between the fluid in the conduit and the ambient surrounding the conduit can be used to power the sources, the sensors and the control unit. It is understood that the temperature from either the fluid in the conduit or the ambient can be used to power the components of this embodiment.

Figure 6:
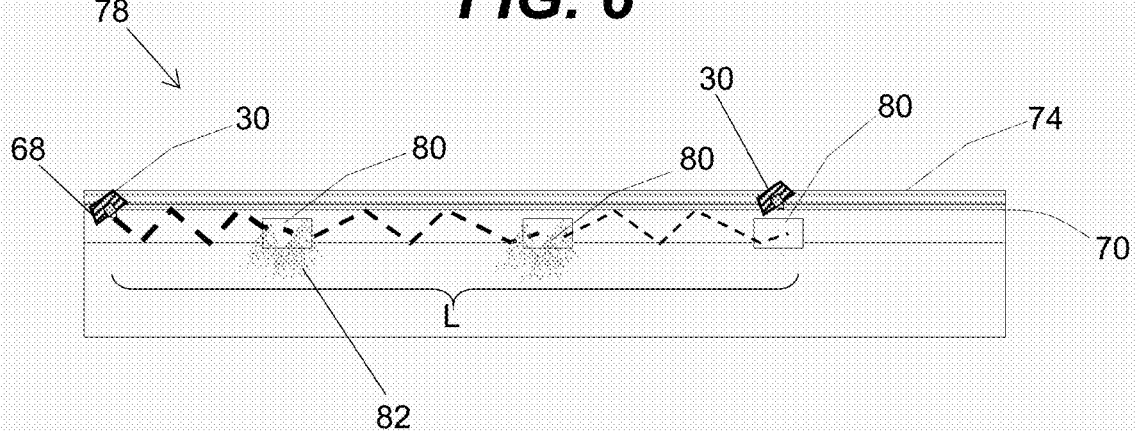
FIG. 6 shows a schematic of a light guiding layer illustrating the attenuation of light generated from an ultraviolet radiation source according to an embodiment.

FIG. 6 shows a schematic of a light guiding layer 78 according to another embodiment in which a set of ultraviolet radiation sources 30 are coupled to a port 68 in a top surface 70 of the light guiding layer with a reflective layer 74 formed over the sources, the port and the top surface. It is understood that in this configuration there can be some attenuation of the light generated from the ultraviolet radiation sources 30. In addition to attenuation, the light guiding layer 78 can experience some leaking of the ultraviolet light due to the finite difference in the refraction indices.

FIG. 6 illustrates the leaking of ultraviolet light that occurs in the light guiding layer 78 as ultraviolet leaking sections 80. As can be seen from FIG. 6, the light is attenuated while it leaks through the light guiding layer 78 at the ultraviolet leaking sections 80, as evidenced in the figure by the fading rays 82 of ultraviolet radiation generated from the ultraviolet radiation source 30 at the left-hand corner of the light guiding layer. FIG. 6 also shows the light rays eventually extinguish after propagating a distance L from the ultraviolet radiation source 30 at the left-hand corner to the source at the right-hand side of the light guiding layer 78.

In one embodiment, each port 68 with an ultraviolet radiation source 30 can be separated from an adjacent port by a distance L, wherein L is the distance that ultraviolet radiation emitted from one ultraviolet radiation source is partially attenuated. As used herein partially attenuated means attenuation not exceeding 20 dB. In one embodiment, L can be the distance that the ultraviolet radiation emitted from one ultraviolet radiation source 30 has an intensity that is at least 30% of the intensity emitted at the location that the ultraviolet radiation source is placed. In another embodiment, L can be the distance between adjacent ultraviolet radiation sources 30, wherein the ultraviolet radiation propagating between the adjacent ultraviolet radiation sources has an intensity at half the distance L/2 of that of the adjacent ultraviolet radiation sources.

Figure 7:
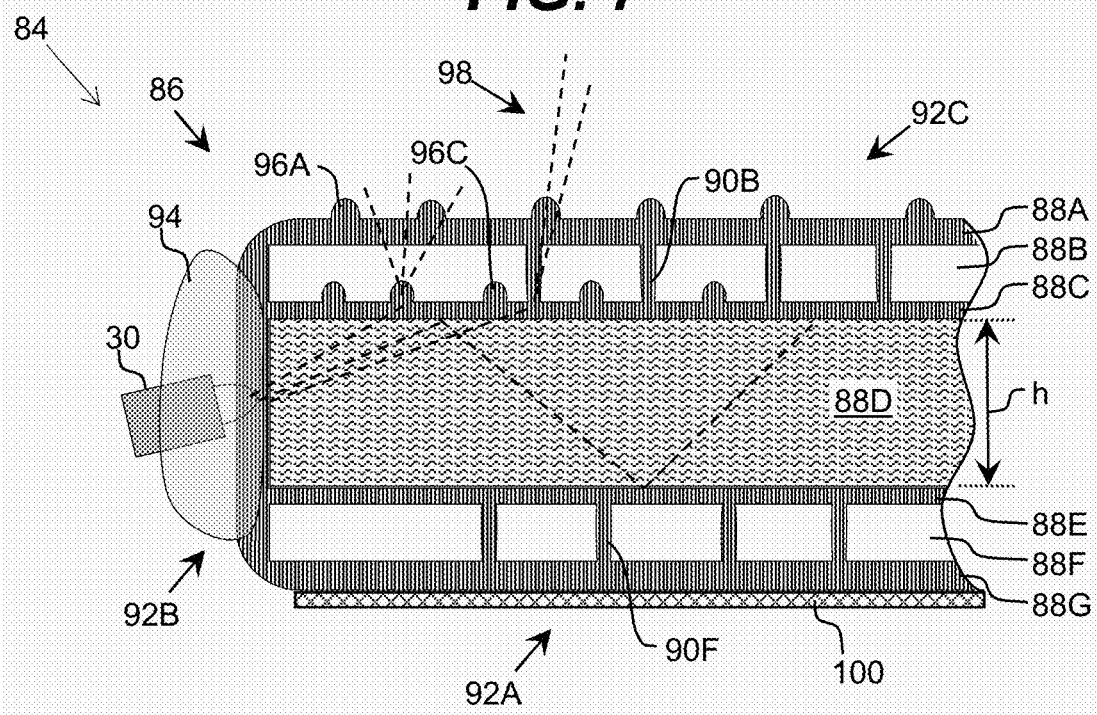
FIG. 7 shows a schematic of a light guiding layer in the form of a waveguide structure according to an embodiment.

FIG. 7 shows a schematic cross-sectional view of a light guiding layer 84 in the form of an alternative waveguide structure 86 according to an embodiment that utilizes total internal reflection (TIR) to propagate light there through. The waveguide structure 86 includes multiple layers 88A-

88G. Layers 88A, 88C, 88E, and 88G can be formed of any suitable type of transparent material. For example, when the radiation is ultraviolet radiation, the material can be an ultraviolet transparent fluoropolymer-based material. Illustrative fluoropolymers capable of being utilized to form the waveguide structure 86 include: fluorinated ethylene-propylene (EFEP), fluorinated ethylene propylene (FEP), perfluoroalkoxy (PFA), tetrafluoroethylene hexafluoropropylene vinylidene fluoride (THV), polytetrafluoroethylene (PTFE), polyvinylidene fluoride (PVDF), ethylene-tetrafluoroethylene (ETFE), ethylene chlorotrifluoroethylene (ECTFE), polychlorotrifluoroethene (PCTFE), a copolymer of tetrafluoroethylene and perfluoromethylvinylether (MFA), low density polyethylene (LDPE), perfluoroether (PFA), an amorphous fluoroplastic resin (e.g., Teflon AF 2400), and/or the like. While primarily described in conjunction with fluoropolymers, it is understood that other comparable materials can be utilized. Illustrative materials include polylactide (PLA), fused silica, sapphire, THE, and/or the like.

Each layer 88A, 88C, 88E, 88G can have a thickness, which is sufficiently thin to provide a desired level of transparency. For example, a layer 88A, 88C, 88E, 88G can be formed of Teflon AF 2400 and have a thickness of several micrometers (e.g., ten micrometers or less) or even several tens of micrometers (e.g., forty micrometers or less). An illustrative solution for fabricating such fluoropolymer layers is shown, for example, in U.S. Pat. No. 7,914,852, which is hereby incorporated by reference. In an embodiment, the fluoropolymer is applied onto a thin layer of fused silica. In an embodiment, selection of the thicknesses and/or refractive indexes of the materials can be performed using a genetic algorithm. In this case, multiple possible combinations of values are evaluated with a subset of the best performing values used, along with some randomness, to create a new group of values to be evaluated. Such a process can be repeated any number of times to arrive at a set of values.

Regardless, the waveguide structure 86 includes layers 88B, 88D, 88F, which are filled with a transparent fluid. In an embodiment, layers 88B, 88F are filled with a transparent gas while the layer 88D is filled with a transparent liquid. In an embodiment, the gas in the layers 88B, 88F can have a low refractive index (e.g., at most ninety percent of the refractive index of the material forming the adjacent layers 88A, 88C, 88E, 88G), such as ambient air. In an embodiment, the liquid in the layer 88D is substantially transparent to ultraviolet radiation. In this case, the liquid has a transparency at least similar (e.g., within ten percent) to the transparency of purified water for light wavelengths in the range of 240 nm to 360 nm. In an embodiment, the liquid in the layer 88D is purified water as defined by the U.S. Food and Drug Administration. Alternatively, the liquid can be water sufficiently clean for human consumption (potable water).

For a layer 88B, 88F including a gas, the waveguide structure 86 can further include a corresponding set of pillars 90B, 90F. The pillars 90B, 90F also can be formed of a fluoropolymer-based material described herein. The pillars 90B, 90F can be configured to maintain a shape of the corresponding low refractive index guiding layer 88B, 88F, respectively. To this extent, the pillars 90B, 90F can be located in any pattern/random arrangement and can have any combination of one or more sizes and/or shapes, which is suitable for providing a desired amount of support. While not shown, it is understood that any fluid-filled layer, such as the layer 88D, can include a set of pillars. In an embodiment, the pillars 90B, 90F comprise diffusive elements. In this case, as illustrated, the diffusive elements start at one layer, such as the layer 88A, extend through a layer 88B, and end at another layer 88C. When both sets of pillars 90B, 90F are included, the pillars 90B can be staggered in relation to the pillars 90F.

As illustrated, a light source 30 (e.g., an ultraviolet radiation emitter) can be coupled to the waveguide structure 86 at a location adjacent to a side 92B of the waveguide structure 86. The coupling mechanism 94 used to attach the light source 30 to the waveguide structure 86 can be configured to hold the light source 30 in a position such that light enters the waveguide structure 86 at an angle optimal for wave guiding, e.g., at an angle larger than the total internal reflection angle for the waveguide structure 86. In an embodiment, at least thirty percent of the light generated by the light source 30 is guided along the layer 88D. In an embodiment, the coupling mechanism 94 is a domain formed of a fluoropolymer-based material described herein, in which the light source 30 is embedded. While only a single light source 30 is shown, it is understood that any number of light sources 30 can be coupled to the waveguide structure 86 in any of various possible combinations of locations.

One or more layers 88A-88G of the waveguide structure 86 can include a set of diffusive elements associated therewith, which are configured to allow light to propagate through the emission surface 92C out of the waveguide structure 86 in a diffusive manner. For example, the layer 88A is shown including a set of diffusive elements 96A, and the layer 88C is shown including a set of diffusive elements 96C. As illustrated, the diffusive elements 96A can be located on an outer surface of the layer 88A forming the emission surface 92C. Embodiments of diffusive elements 96A, 96C described herein can have any of various shapes including: a truncated cone, a lens, a sphere, a pyramid, an inverted truncated cone, an inverted pyramid, and/or the like. Furthermore, it is understood that a set of diffusive elements 96A, 96C can include a combination of diffusive elements of two or more different shapes. The diffusive elements 96A, 96C can be formed using any solution, such as surface patterning or roughening, welding/fusing the diffusive elements 96A, 96C to the corresponding layer 96A, 96C, and/or the like.

In an embodiment, each diffusive element 96A, 96C is capable of diffusive transmission/reflection of the ultraviolet radiation 98 approximating a Lambertian distribution. In particular, an angular distribution of intensity of ultraviolet radiation 98 transmitted/reflected from the diffusive element 96A, 96C can be normalized by total emitted power and compared to the Lam bertian distribution. As used herein, the distribution approximates a Lambertian distribution when the deviation from the Lambertian distribution at each emitted angle is less than forty percent. The distribution substantially approximates a Lam bertian distribution when the deviation is less than ten percent from a Lam bertian distribution at each emitted angle. Furthermore, a distance between two adjacent diffusive elements 96A, 96C located on a surface can be selected to be smaller than an effective area of a surface illuminated by the diffusive ultraviolet radiation 98 transmitted/reflected by the diffusive elements 96A, 96C. To this extent, the spacing can be determined based on the distribution of the ultraviolet radiation 98 from a diffusive element 96A, 96C as well as a target distance between the diffusive element 96A, 98C and a surface of an object being illuminated. Furthermore, when implemented as part of a disinfection system as described herein, spacing between adjacent diffusive elements 96A, 96C can be determined based on an expected spatial density of contamination on a surface to be disinfected. In this case, the distance can be inversely proportional to the expected spatial density of contamination.

Additionally, one or more of the layers 88A, 88C, 88E, and 88G can be formed of and/or coated with a reflective material. When utilized, a reflective coating can be located over an entirety of the layers 88A, 88C, 88E, and 88G, or only a portion of the layers 88A, 88C, 88E, and 88G. Furthermore, the reflective coating can be located on either the outermost or innermost surface of the layers 88A, 88C, 88E, and 88G. For example, the layer 88G can include a reflective coating on an outermost surface of the layer 88G. However, it is understood that this is only illustrative. To this extent, depending on the application, any surface of the waveguide structure 86 can contain a reflective coating. The reflective coating can be applied using any solution, such as evaporating a reflective metal (e.g., aluminum), coating with a reflective polymer (e.g., Teflon), and/or the like. In an embodiment, the reflective coating can be formed of a highly reflective material, such as highly polished aluminum, and/or the like. In a more particular embodiment, the reflective coating can be formed of a diffusively reflective material, such as a highly ultraviolet reflective expanded polytetrafluoroethylene (ePTFE) membrane (e.g., GORE® Diffuse Reflector Material), and/or the like.

In an embodiment, the material forming the reflective coating 100 is selected based on one or more optical characteristics of the waveguide structure 86. For example, the reflective coating 100 can be selected such that the reflectivity of the material is comparable to the transparency of the layers 88A, 88C, 88E, 88G within the waveguide structure 86. Furthermore, the layers 88A, 88C, 88E, 88G can be partially reflective and partially transparent and a small ultraviolet absorption. It is understood that ultraviolet absorption can be minimized, subject to other optimization parameters. Regardless, an ETFE film, such as Fluon® ETFE Film, has as much as ninety percent transmission for ultraviolet rays in the range of 280 nm to 360 nm. In this case, the reflective coating 100 can be formed of a material having a reflectivity of approximately ninety percent (+/− five percent). It is understood that embodiments of the waveguide structure 86 can include various combinations of other devices, which can be used to redirect, diffuse, wave guide, recirculate, and/or the like, the light emitted by the ultraviolet radiation source 30. Illustrative additional devices include one or more reflectors/mirrors, a reflective/transparent mesh, and/or the like.

A spacing between two or more ultraviolet radiation sources 30 can be determined based on one or more attributes of the waveguide structure 86. For example, for a light ray propagating at the total internal reflection (TIR) angle of approximately fifty degrees, a distance that the light ray propagates within the fluid in the layer 88D of the waveguide structure 86 between collisions with the walls 88C, 88E of the waveguide structure 86 is about 1.2*h, where h is the thickness of the layer 88D of the waveguide structure 86. The light ray will lose approximately fifty percent of its intensity after approximately six collisions with the walls 88C, 88E, which corresponds to an overall lateral distance on the order of 7*h. For retention of at least thirty percent of the intensity, the lateral distance of travel can be as much as 13*h. For example, for a thickness h of one millimeter, a lateral distance of travel of a light ray of approximately 1.3 centimeters will deliver an intensity of about thirty percent for the light propagating at an angle of fifty degrees to a surface normal of the walls 88C, 88E of the waveguide structure 86. Based on a desired intensity and uniformity of the illumination, as well as optical properties of the waveguide structure 86, the spacing between two or more ultraviolet radiation sources 30 can be readily determined. In an embodiment, a thickness of the layer 88D is at most ten percent of a length of the layer 88D.

Light rays propagating at greater than the TIR angle can travel further while retaining a comparable intensity (due to less frequent collisions with the walls 88C, 88E). In an embodiment, an ultraviolet radiation source 30 is configured to emit light at least partially collimated in a direction of the waveguide structure 86. In this case, most of the light emitted by the ultraviolet radiation source 30 will collide with the walls 88C, 88E at angles significantly larger than the TIR angle. At least partial collimation of the light emitted by the ultraviolet radiation source 30 can be achieved using any solution. For example, the emitting properties of an LED included in the ultraviolet radiation source 30 can be modified/selected to emit at least partially collimated light (e.g., a laser diode can be utilized), an LED can be combined with a reflector (e.g., parabolic reflector, conic reflector, truncated pyramid reflector, and/or the like) to at least partially collimate the light, and/or the like. Additional details of a waveguide structure are found in U.S. patent application Ser. No. 14/853,075, which is hereby incorporated by reference.

FIG. 8 shows a schematic of a fluid transport conduit 102 having ultraviolet transparent sections 104 that include ultraviolet transparent windows 105 and ultraviolet transparent domains 107 proximate to the windows according to embodiment. The ultraviolet transparent windows 105 and the ultraviolet transparent domains 107 can enable ultraviolet light penetration and guiding there through. As shown in FIG. 8, the ultraviolet transparent sections 104 of the fluid transport conduit 102 can align with the ports 68 of a light guiding layer 106 that encloses the conduit. The ultraviolet radiation sources 30 that are coupled to the ports 68 of the light guiding layer 106 can transmit ultraviolet radiation that passes through the ultraviolet transparent windows 105 and the ultraviolet transparent domains 107 into the interior of the fluid transport conduit 102. In this manner, the ultraviolet radiation can irradiate the internal walls 108 of the fluid transport conduit 102. It is understood that in this embodiment only a fraction of the surface of the fluid transport conduit 102 can be covered by the light guiding layer 106.

In one embodiment, the irradiation of the internal walls 108 can be facilitated by a set of diffusive ultraviolet reflective elements 110 placed about the ultraviolet transparent sections 104, and a diffusive ultraviolet reflective layer 112 on a surface of the fluid transport conduit 102 that opposes the set of diffusive ultraviolet reflective elements 110 and the ultraviolet transparent sections 104. In one embodiment, the diffusive ultraviolet reflective elements 110 and the diffusive ultraviolet reflective layer 112 can include any of the aforementioned diffusive ultraviolet materials.

As shown in FIG. 8, the set of diffusive ultraviolet reflective elements 110 can align with a set of reflective elements 114 that abut both sides of each of the ports 68 formed in the light guiding layer 106. The light guiding layer 106 can also include a reflective layer 116 on an opposing surface that covers the diffusive ultraviolet reflective layer 112 of the fluid transport conduit 102. Both the set of reflective elements 114 and the reflective layer 116 can include any of the aforementioned reflective materials.

In one embodiment, as shown in FIG. 8, a sensor 64 can be coupled to one or more ports 68 of the light guiding layer 106 in order to monitor one of the operating parameters used in the disinfection of the internal walls 108 of the fluid transport conduit 102. As shown in FIG. 8, the sensor 64 can extend from the port 68 of the light guiding layer 106 into a region of the fluid transport conduit 102 that would cover an ultraviolet transparent section 104 if an ultraviolet radiation source were to be coupled thereto. It is understood that any of the aforementioned sensors are suitable for use in this embodiment. The single sensor 64 depicted in FIG. 8 is only illustrative and it is understood that more sensors can be deployed if desired.

The components of both the fluid transport conduit 102 and the light guiding layer 106 are only illustrative, and it is understood that these items can include additional components. For example, the light guiding layer 106 can comprise other sub-layers in addition to the set of reflective elements 114 and the reflective layer 116. In one embodiment, the light guiding layer 106 can include a sub-layer that delivers power from a power source to the ultraviolet radiation sources 30, the sensor 64, and a control unit (not depicted).

FIG. 9 shows a schematic of a fluid transport conduit 118 and a light guiding layer 120 formed of a flexible material according to embodiment. The flexible material used for the fluid transport conduit 118 and the light guiding layer 120 can include, but is not limited to a fluoropolymer film. In one embodiment, the fluid transport conduit 118 and the light guiding layer 120 can include the flexible material at regions where there are no ultraviolet radiation sources 30. For example, the flexible material can be used at regions outside of the ports 68 where the ultraviolet radiation sources 30 are coupled to emit ultraviolet radiation through the ultraviolet window 105 into the fluid transport conduit 118. In this manner, the fluid transport conduit 118 and the light guiding layer 120 can have a bending configuration, while the regions of the light guiding layer 120 that have the ports 68 and the ultraviolet radiation sources 30 coupled thereto, and the ultraviolet window 105 of the fluid transport conduit 118 can form rigid domains.

Figure 10A:
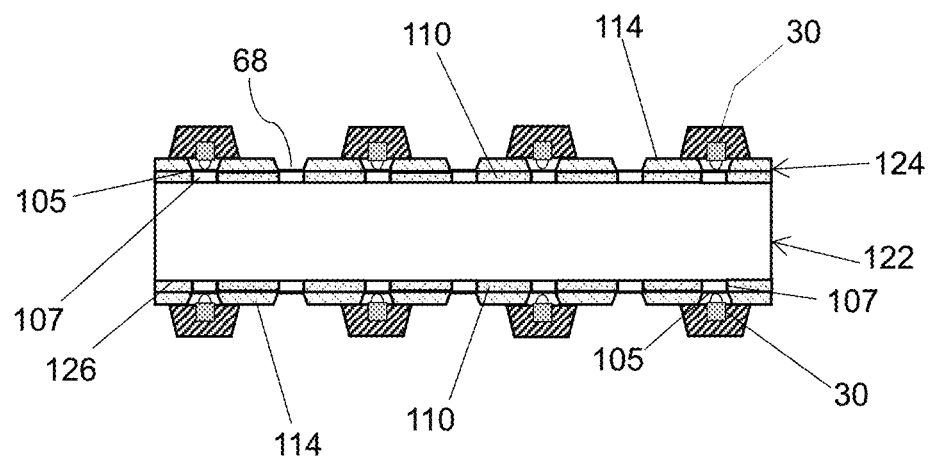
FIGS. 10A-10B illustrate an example of a distribution of a set of ultraviolet radiation sources over a surface of a fluid transport conduit and a light guiding layer that encloses the conduit according to an embodiment.
Figure 10B:
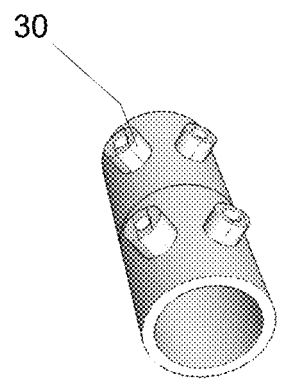

FIGS. 10A-10B illustrate an example of a possible distribution of a set of ultraviolet radiation sources 30 over a surface of a fluid transport conduit 122 and a light guiding layer 124 that encloses the conduit according to an embodiment. As shown in FIG. 10A, the fluid transport conduit 122 can have ultraviolet transparent windows 105 and ultraviolet transparent domains 107 proximate to the windows. The ultraviolet transparent windows 105 and the ultraviolet transparent domains 107 can enable ultraviolet light penetration and guiding there through for ultraviolet radiation emitted from an ultraviolet radiation source 30. The ultraviolet transparent windows 105 and the ultraviolet transparent domains 107 can align with the ports 68 of a light guiding layer 124 that encloses the conduit. A set of diffusive ultraviolet reflective elements 110 can be placed about the ultraviolet transparent windows 105 and the ultraviolet transparent domains 107. The set of diffusive ultraviolet reflective elements 110 can align with a set of reflective elements 114 that abut both sides of each of the ports 68 formed in the light guiding layer 124.

In this configuration, the ultraviolet radiation sources 30 that are coupled to the ports 68 of the light guiding layer 124 can transmit ultraviolet radiation that passes through the ultraviolet transparent windows 105 and the ultraviolet transparent domains 107 into the interior of the fluid transport conduit 122. In this manner, the ultraviolet radiation can irradiate the internal walls 126 of the fluid transport conduit 102.

In comparison to the embodiment depicted in FIG. 8 in which the ultraviolet radiation sources 30 are disposed along only a limited portion of the surface area of the fluid transport conduit, the configuration of FIGS. 10A-10B shows that the sources can be distributed over all of a surface area of the fluid transport conduit 122. As shown in the cross-sectional view of FIG. 10A, the fluid transport conduit 122 can have the transparent windows 105, the ultraviolet transparent domains 107, and the diffusive ultraviolet reflective elements 110 positioned about the ports 68 and the reflective elements 114 of the light guiding layer 124 for all of the ultraviolet radiation sources 30 that are coupled to the light guiding layer.

Having the ultraviolet radiation sources 30 distributed over all of a surface area of the fluid transport conduit 122 may provide a more effective cleaning and removal of contaminants from the internal walls 126 of the conduit because there is more extensive coverage of the walls from the various positioned sources. In comparison to the configuration depicted in FIG. 8, there will be less coverage of the internal walls because the ultraviolet radiation sources generally extend uniformly in an axial direction from a first end of the fluid transport conduit to an opposing second of end of the fluid transport conduit. However, the diffusive ultraviolet reflective layer and the reflective placed on the opposing sides of the fluid transport conduit and the light guiding layer, respectively, in FIG. 8 can promote recycling of light within the conduit to facilitate effective cleaning of the internal walls.

The embodiment illustrated in FIGS. 10A-10B is meant to illustrate that the ultraviolet radiation sources 30 can be distributed in a manner that includes a larger surface area of the light guiding layer 124 in order to attain a more extensive coverage of the internal walls 126 of the fluid transport conduit 122 that is cleaned. It is understood that this embodiment can include a variety of other components that facilitate the cleaning of the internal walls 126 including removal of contaminants that form on the walls. For example, any of the aforementioned sensors, as well as the control unit can be implemented in this configuration to facilitate the treatment of the internal walls 126 of the fluid transport conduit 122.

Figure 11A:
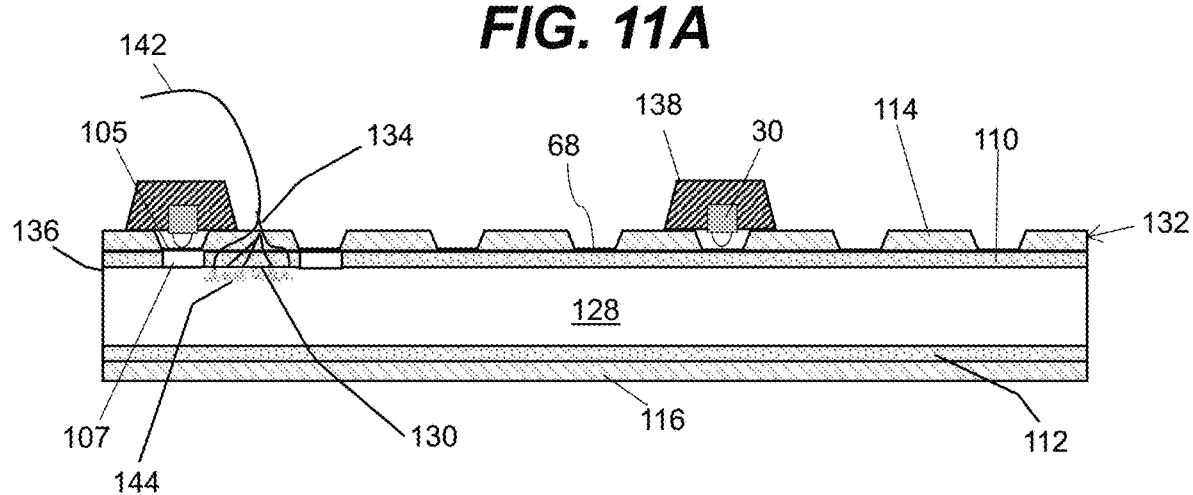
FIGS. 11A-11B illustrate a schematic of a fluid transport conduit having a porous section, and a light guiding layer having a fluid intake port to deliver a cleansing fluid to the internal walls of the conduit via the porous section according to an embodiment.
Figure 11B:
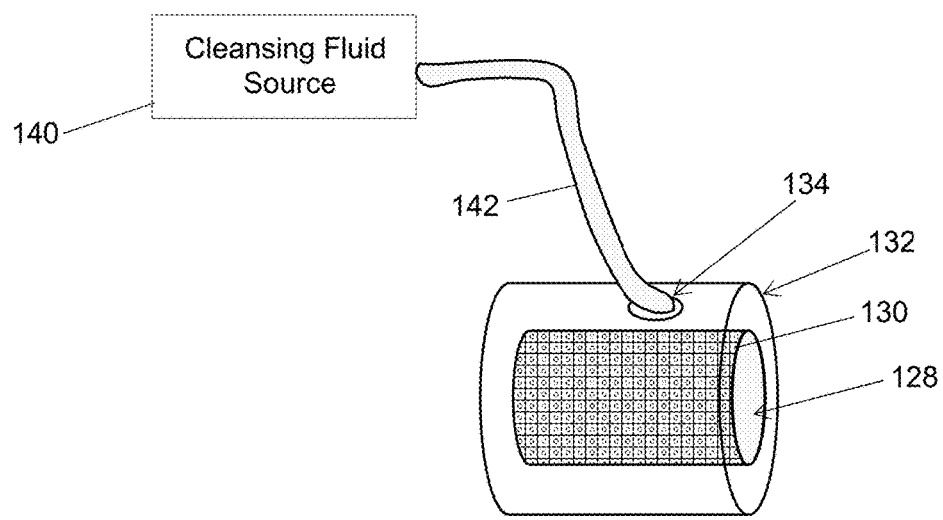

FIGS. 11A-11B illustrate a schematic of fluid transport conduit 128 having a porous section 130, and a light guiding layer 132 having a fluid intake port 134 to deliver a cleansing fluid to the internal walls 136 of the conduit according to an embodiment. As shown in FIG. 11A, the fluid transport conduit 128 can have ultraviolet transparent windows 105 and ultraviolet transparent domains 107 proximate to the windows. The fluid transport conduit 128 can also have a layer of diffusive ultraviolet reflective elements 110 positioned between the ultraviolet transparent windows 105 and the ultraviolet transparent domains 107. The ultraviolet transparent windows 105 and the ultraviolet transparent domains 107 of the fluid transport conduit 128 can align with the ports 68 of a light guiding layer 132 that encloses the conduit. The fluid transport conduit 128 can further include a diffusive ultraviolet reflective layer 112 on a surface that opposes the layer of diffusive ultraviolet reflective elements 110, the ultraviolet transparent windows 105 and the ultraviolet transparent domains 107. The light guiding layer 132 can include a reflective layer 116 on a surface opposing the layer of diffusive ultraviolet reflective elements 114 and the ports 68 that covers the diffusive ultraviolet reflective layer 112.

As shown in FIG. 11A, some of the ports 68 of the light guiding layer 132 can be coupled to an ultraviolet radiation source 30 with a reflective element 138 encapsulating the source and the port. The reflective element 138, which can include any of the aforementioned reflective materials can encapsulate a corresponding ultraviolet radiation source 30 and port 68, and extend onto adjacent segments of the diffusive ultraviolet reflective elements 114. It is understood that the number of ports 68 in the light guiding layer 132 with coupled ultraviolet radiation sources 30 is only illustrative of one possible configuration and is not meant to be limiting.

In this embodiment, like others described herein, the ultraviolet radiation sources 30 that are coupled to the ports 68 of the light guiding layer 132 can transmit ultraviolet radiation that passes through the ultraviolet transparent windows 105 and the ultraviolet transparent domains 107 into the interior of the fluid transport conduit 128. In this manner, the ultraviolet radiation can irradiate the internal walls 136 of the fluid transport conduit 128.

In addition to the use of ultraviolet radiation sources 30 to irradiate the internal walls 136 of the fluid transport conduit 128, the embodiment of FIGS. 11A-11B can utilize a cleansing fluid source 140 having a cleansing fluid, such as for example, liquid soap to clean the walls. In this embodiment, the cleansing fluid source 140 can supply the cleansing fluid to the fluid intake port 134 via a cleansing fluid channel 142. In one embodiment, the cleansing fluid channel 142 can include a tube or hose that can connect with both the cleansing fluid source 140 and the fluid intake port 134 of the light guiding layer 132.

In this manner, the fluid intake port 134 can deliver the cleansing fluid to the porous section 130 of the fluid transport conduit 128. In one embodiment, the porous section 130 can extend from the outer surface of the fluid transport conduit 128 to the internal walls 136 of the fluid transport conduit. In addition, the porous section 130 can include any material that is sufficient to permit the transfer of fluid from one surface to another. For example, the porous section 130 can include, but is not limited to, material such as alumina. In one embodiment, the porous section 130 can include a multitude of pores each with diameters ranging from 10 microns to 1 mm. This enables the porous section 130 to generate a pressurized shower 144 of cleansing fluid as the fluid from the cleansing fluid source 140 is delivered into the fluid transport conduit 128. This pressurized shower 144 of cleansing fluid can dislodge any contaminants that have accumulated on the internal walls 136 of the fluid transport conduit 128. Although FIG. 11A only discloses one porous section 130 in the fluid transport conduit 128, it is understood that there can be more than one section in the conduit that can be used to deliver a pressurized shower of cleansing fluid to the internal walls 136 of the fluid transport conduit 128.

The use of the cleansing fluid source 140, the cleansing fluid channel 142, the fluid intake port 134, and the porous section 130 to clean the internal walls 136 of the fluid transport conduit 128 can operate with the ultraviolet radiation sources 30 in a variety of implementations. For example, the cleansing fluid source 140, the cleansing fluid channel 142, the fluid intake port 134, and the porous section 130 can operate simultaneously with the ultraviolet radiation sources 30. In another embodiment, the cleansing fluid source 140, the cleansing fluid channel 142, the fluid intake port 134, and the porous section 130 can operate prior to, or after an application of ultraviolet light generated from the ultraviolet radiation sources 30.

It is understood that this embodiment depicted in FIGS. 11A-11B can include a variety of other components that facilitate the cleaning of the internal walls 136 of the fluid transport conduit 128. For example, any of the aforementioned sensors as well as the control unit can be implemented in this configuration to facilitate the treatment of the internal walls 138 of the fluid transport conduit 128.

Figure 12:
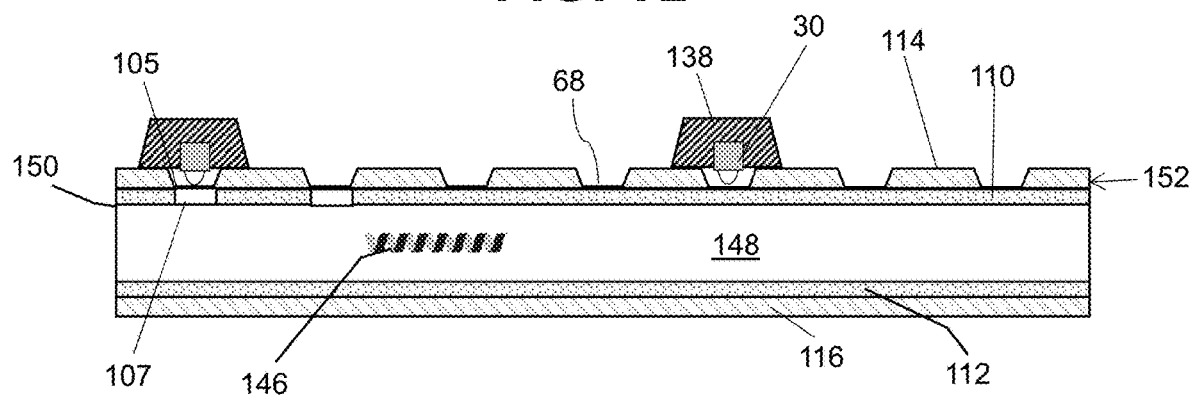
FIG. 12 shows a schematic of a cleansing mixing unit configured to impart a mixing action to fluid delivered in a fluid transport conduit in order to clean the internal walls of the conduit according to an embodiment.

FIG. 12 shows a schematic of an embodiment in which another cleaning modality operates in conjunction with the set of ultraviolet radiation sources 30. In this embodiment, a cleansing mixing unit 146 is configured to impart a mixing action to the fluid delivered in a fluid transport conduit 148 in order to clean the internal walls 150 of the conduit. The mixing action generated by the cleansing mixing unit 146 promotes dislodgment of contaminants that have accumulated on the internal walls of the fluid transport conduit 148. The cleansing mixing unit 146 can include, but is not limited to, wall jets, tubular mechanical cleaning inserts, and mixing fans. In one embodiment, the cleansing mixing unit 146 can be located within the fluid transport conduit 148. For example, the cleansing mixing unit 146 can be placed in the fluid flow path of the fluid transport conduit 148 by a fixed holder (not illustrated in FIG. 12). It is understood that the cleansing mixing unit 146 can be disposed in other locations of the fluid transport conduit 148. Also, it is understood that the fluid transport conduit 148 can have more than one cleansing mixing unit disposed in the conduit.

The cleansing mixing unit 146 can operate in conjunction with the ultraviolet radiation sources 30 coupled to the ports 68 of a light guiding layer 152 that encloses the fluid transport conduit 148. Note that in this embodiment, the fluid transport conduit 148 and the light guiding layer 152 can include the same elements as those contained in the fluid transport conduit 128 and the light guiding layer 132 of FIGS. 11A-11B, except that the fluid transport conduit 148 and the light guiding layer 152 of FIG. 12 do not have a porous section and a fluid intake port, respectively. However, it is understood, these elements along with a cleansing fluid source 140 (FIGS. 11A-11B) and a cleansing fluid channel 142 (FIGS. 11A-11B) can be used to complement the treatment of the internal walls 150 of the fluid transport conduit 148 by the ultraviolet radiation sources 30 and the cleansing mixing unit 146.

In operation, the ultraviolet radiation sources 30, that are coupled to the ports 68 of the light guiding layer 152, can transmit ultraviolet radiation that passes through the ultraviolet transparent windows 105 and the ultraviolet transparent domains 107 into the interior of the fluid transport conduit 148. In this manner, the ultraviolet radiation can irradiate the internal walls 150 of the fluid transport conduit 148. Simultaneously, or at another time in which the ultraviolet radiation sources 30 are emitting ultraviolet radiation to irradiate the internal walls 150, the cleansing mixing unit 146 can impart a mixing action onto the fluid delivered in the fluid transport conduit 148 that is sufficient to dislodge any contaminants that have accumulated on the internal walls.

It is understood that this embodiment depicted in FIG. 12 can include a variety of other components that facilitate the cleaning of the internal walls 150 of the fluid transport conduit 148. For example, other cleaning modalities can be used to complement the treatment of the internal walls 150 in the fluid transport conduit 148. In one embodiment, a non-biofouling material can be applied to the internal walls 150 of the fluid transport conduit 148. Examples of a non-biofouling material that can be applied to the internal walls 150 of the fluid transport conduit 148 can include, but are not limited to, an ultra-low fouling surface with "slippery" nanoscale topology, similar to a dolphin skin. In another embodiment, at least a portion of the internal walls 150 of the fluid transport conduit 148 can include an ultraviolet photo-catalyst that enhances the effect of the ultraviolet radiation. The ultraviolet photo-catalyst can include metal or semiconductor nanoparticles to stimulate plasmonic photocatalysis. Other examples of an ultraviolet photo-catalyst can include, but are not limited to, ITO. In another embodiment, a chemical de-scaler can operate in conjunction with the ultraviolet radiation sources 30 and/or the cleansing mixing unit 146 to chemically remove scale from the internal walls of the fluid transport conduit. Examples of a chemical de-scaler that is suitable for use can include, but is not limited to, citric acid.

In another embodiment, at least one visible camera can be deployed in the fluid transport conduit 148 or the light guiding layer 152. The camera along with at least one sensor and a control unit can be used to determine an amount of scale contamination on the internal walls 150 of the fluid transport conduit 148. In this manner, the control unit can control the cleaning treatment of the internal walls 150 by the ultraviolet radiation sources 30, the cleansing mixing unit 146, or any other cleaning modality that is used.

Figure 13:
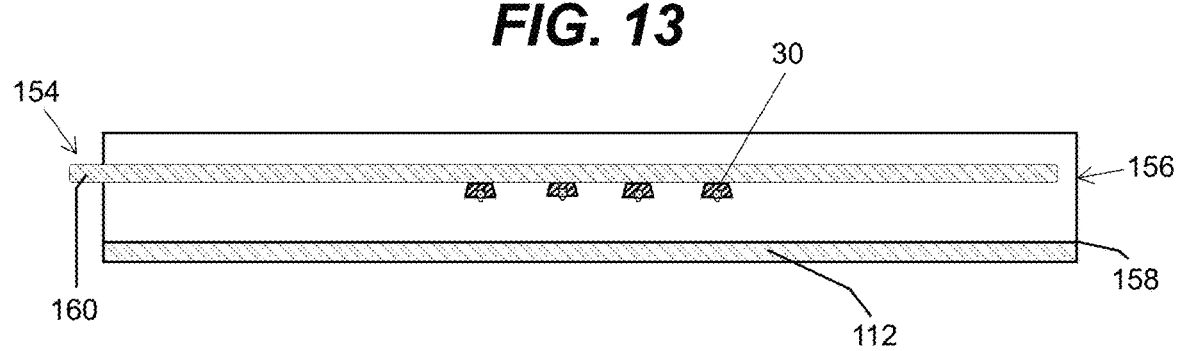
FIG. 13 shows a schematic of an ultraviolet insert module having a set of ultraviolet radiation sources that can be inserted into a fluid transport conduit to directly irradiate the internal walls of the conduit according to an embodiment.

In the embodiments described heretofore, the set of ultraviolet radiation sources 30 have been coupled to a light guiding layer and configured to emit ultraviolet light that penetrates through ultraviolet windows formed in a fluid transport conduit. However, it is understood that the set of ultraviolet radiation sources 30 can be configured to irradiate the internal walls of the ultraviolet fluid transport conduit using other approaches. For example, FIG. 13 shows a schematic of an ultraviolet insert module 154 having a set of ultraviolet radiation sources 30 that can be inserted into a fluid transport conduit 156 to directly irradiate the internal walls 158 of the conduit according to an embodiment. In one embodiment, the ultraviolet insert module 154 can include an ultraviolet radiation source supporting member 160 that supports the set of ultraviolet radiation sources 30. The ultraviolet radiation source supporting member 160 can include any ultraviolet transparent element that can support the ultraviolet radiation sources 30 and that can be placed with a fluid transport conduit. Examples of an ultraviolet radiation source supporting member can include, but are not limited to, a stainless-steel support.

In operation, the ultraviolet insert module 154 can be placed within the fluid transport conduit 156 and directed to emit ultraviolet radiation towards the surface of the internal walls 158 of the conduit. In this manner, the ultraviolet radiation emitted from the ultraviolet radiation sources 30 can irradiate the internal walls 158, dislodging any contaminants that may have accumulated on the walls. The reflective layer 112 of the fluid transport conduit 156 can recycle the radiation within the fluid transport conduit 156. This allows the radiation to reflect off the internal walls 158 of the fluid transport conduit 156, thereby promoting the removal of contaminants from all of the walls within the conduit. In one embodiment, the ultraviolet insert module 154 is configurable to be rotated within the fluid transport conduit 156. This allows the ultraviolet radiation emitted from the ultraviolet radiation sources 30 to be directed directly towards an opposing internal wall surface.

Other modular approaches can be used to irradiate the internal walls of an ultraviolet fluid transport conduit. For example, as shown in FIGS. 14A-14B, a disinfection module 162 can be coupled to various portions of a fluid transport conduit 164 to clean those specific sections of the conduit and those sections located nearby. In one embodiment, the disinfection module 162 can include a set of ultraviolet radiation sources, a light guiding unit, and a power source (all not shown). In this manner, the ultraviolet radiation sources controlled by the control unit and powered by the power source, can emit ultraviolet radiation that the light guiding unit guides to the internal walls of the fluid transport conduit 164 for treatment thereof. It is understood, the disinfection module 162 can include other components such as any of the aforementioned sensors.

The disinfection module 162 can be coupled to the fluid transport conduit 164 by the use of a set of fasteners 166. The fasteners 166 can include one of a variety of fittings that can form a cross-connection between two adjacent sections of a fluid transport conduit. In embodiments, wherein the fluid transport conduit takes the form of piping, the fasteners 166 can include pipe fittings and connectors made from a variety of material including, but not limited to, PVC, polypropylene, polyethylene, steel, brass and copper. The fasteners 166 enable the disinfection module 162 to be installed at various parts of the fluid transport conduit 164. As shown in FIG. 14A, the disinfection module 162 can take the form of a straight segment, or as shown in FIG. 14B, as a bended segment. Both the straight and bended segments can be cross-connected with adjacent sections of the fluid transport conduit 164 through the use of the fasteners. In operation, the disinfection module 162 can be directed to provide an ultraviolet treatment of the internals walls of the fluid transport conduit 164 that are located proximate. It is understood that the lighting guiding unit of the disinfection module 162 can guide and direct the ultraviolet radiation to sections of the fluid transport conduit 164 that are further removed from the location of the module.

FIG. 15 shows a schematic of an ultraviolet cleaning unit 800 that can be implemented with any of the embodiments depicted in FIGS. 2-14 according to an embodiment. In this embodiment, the ultraviolet cleaning unit 800 is shown including the ultraviolet radiation sources 30 (UV radiation source(s)) and the sensors 64 for the purposes of illustrating the interaction of all of the components that are used to provide a cleaning treatment to the internal walls of a fluid transport conduit.

As depicted in FIG. 15, the cleaning unit 800 can include a control unit 805. In one embodiment, the control unit 805 can be implemented as a computer system 820 including an analysis program 830, which makes the computer system 820 operable to manage the ultraviolet radiation sources 30 and the sensors 64 in the manner described herein. In particular, the analysis program 830 can enable the computer system 820 to operate the ultraviolet radiation sources 30 to generate and direct ultraviolet radiation towards the internal walls of the fluid transport conduit and process data corresponding to one or more attributes regarding the walls of the conduit, which can be acquired by the sensors 64, and/or an ultraviolet radiation history stored as data 840. The computer system 820 can individually control each ultraviolet radiation source 30 and sensor 64 and/or control two or more of the ultraviolet radiation sources and the sensors as a group. Furthermore, the ultraviolet radiation sources 30 can emit ultraviolet radiation of substantially the same wavelength or of multiple distinct wavelengths.

In an embodiment, during an initial period of operation, the computer system 820 can acquire data from at least one of the sensors 64 regarding one or more attributes of the internal walls of the fluid transport conduit and generate data 840 for further processing. The data 840 can include information regarding a presence of contaminants (e.g., scale) and biological activity (e.g., microorganisms, viruses, bacteria, and/or the like) on the interior walls of the fluid transport conduit, a frequency of usage of the conduit, a disinfection schedule history for the conduit, an amount of radiation (e.g., ultraviolet, infrared, visible, and/or microwave) detected, and/or the like. The computer system 820 can use the data 840 to control one or more aspects of the ultraviolet radiation generated by the ultraviolet radiation source(s) 30 during a cleaning treatment.

Furthermore, one or more aspects of the operation of the ultraviolet radiation sources 30 can be controlled or adjusted by a user 812 via an external interface I/O component 826B. The external interface I/O component 826B can be located on the exterior of the ultraviolet cleaning unit 800, and used to allow the user 812 to selectively turn on/off the ultraviolet radiation sources 30.

The external interface I/O component 826B can include, for example, a touch screen that can selectively display user interface controls, such as control dials, which can enable the user 812 to adjust one or more of: an intensity, scheduling, and/or other operational properties of the set of ultraviolet radiation sources 30 (e.g., operating parameters, radiation characteristics). In an embodiment, the external interface I/O component 826B could conceivably include a keyboard, a plurality of buttons, a joystick-like control mechanism, and/or the like, which can enable the user 812 to control one or more aspects of the operation of the set of ultraviolet radiation sources 30. The external interface I/O component 826B also can include any combination of various output devices (e.g., an LED, a visual display), which can be operated by the computer system 820 to provide status information pertaining to a cleaning treatment of the fluid transport conduit for use by the user 812. For example, the external interface I/O component 826B can include one or more LEDs for emitting a visual light for the user 812, e.g., to indicate a status of the cleaning treatment. In an embodiment, the external interface I/O component 826B can include a speaker for providing an alarm (e.g., an auditory signal), e.g., for signaling that ultraviolet radiation is being generated or that a cleaning treatment has finished.

The computer system 820 is shown including a processing component 822 (e.g., one or more processors), a storage component 824 (e.g., a storage hierarchy), an input/output (I/O) component 826A (e.g., one or more I/O interfaces and/or devices), and a communications pathway 828. In general, the processing component 822 executes program code, such as the analysis program 830, which is at least partially fixed in the storage component 824. While executing program code, the processing component 822 can process data, which can result in reading and/or writing transformed data from/to the storage component 824 and/or the I/O component 826A for further processing. The pathway 828 provides a communications link between each of the components in the computer system 820. The I/O component 826A and/or the external interface I/O component 826B can comprise one or more human I/O devices, which enable a human user 812 to interact with the computer system 820 and/or one or more communications devices to enable a system user 812 to communicate with the computer system 820 using any type of communications link. To this extent, during execution by the computer system 820, the analysis program 830 can manage a set of interfaces (e.g., graphical user interface(s), application program interface, and/or the like) that enable human and/or system users 812 to interact with the analysis program 830. Furthermore, the analysis program 830 can manage (e.g., store, retrieve, create, manipulate, organize, present, etc.) the data, such as data 840, using any solution.

In any event, the computer system 820 can comprise one or more general purpose computing articles of manufacture (e.g., computing devices) capable of executing program code, such as the analysis program 830, installed thereon. As used herein, it is understood that "program code" means any collection of instructions, in any language, code or notation, that cause a computing device having an information processing capability to perform a particular function either directly or after any combination of the following: (a) conversion to another language, code or notation; (b) reproduction in a different material form; and/or (c) decompression. To this extent, the analysis program 830 can be embodied as any combination of system software and/or application software.

Furthermore, the analysis program 830 can be implemented using a set of modules 832. In this case, a module 832 can enable the computer system 820 to perform a set of tasks used by the analysis program 830, and can be separately developed and/or implemented apart from other portions of the analysis program 830. When the computer system 820 comprises multiple computing devices, each computing device can have only a portion of the analysis program 830 fixed thereon (e.g., one or more modules 832). However, it is understood that the computer system 820 and the analysis program 830 are only representative of various possible equivalent monitoring and/or control systems that may perform a process described herein with regard to the control unit, the ultraviolet radiation sources and the sensors. To this extent, in other embodiments, the functionality provided by the computer system 820 and the analysis program 830 can be at least partially implemented by one or more computing devices that include any combination of general and/or specific purpose hardware with or without program code. In each embodiment, the hardware and program code, if included, can be created using standard engineering and programming techniques, respectively. In another embodiment, the control unit can be implemented without any computing device, e.g., using a closed loop circuit implementing a feedback control loop in which the outputs of one or more sensors are used as inputs to control the operation of the cleaning treatment. Illustrative aspects of the invention are further described in conjunction with the computer system 820. However, it is understood that the functionality described in conjunction therewith can be implemented by any type of monitoring and/or control system.

Regardless, when the computer system 820 includes multiple computing devices, the computing devices can communicate over any type of communications link. Furthermore, while performing a process described herein, the computer system 820 can communicate with one or more other computer systems, such as the user 812, using any type of communications link. In either case, the communications link can comprise any combination of various types of wired and/or wireless links; comprise any combination of one or more types of networks; and/or utilize any combination of various types of transmission techniques and protocols.

All of the components depicted in FIG. 15 can receive power from a power source 845. The power source 845 can take the form of one or more batteries, a vibration power generator that can generate power based on magnetic inducted oscillations or stresses developed on a piezoelectric crystal, a wall plug for accessing electrical power supplied from a grid, and/or the like. In an embodiment, the power source can include a super capacitor that is rechargeable. Other power components that are suitable for use as the power source can include solar, a mechanical energy to electrical energy converter such as a rechargeable device, etc.

FIG. 16 shows a schematic of an illustrative environment 900 in which the ultraviolet cleaning unit 800 depicted in FIG. 15 can be used to facilitate a cleaning treatment of the internal walls of a fluid transport conduit according to an embodiment. In this embodiment, the computer system 820 of the control unit 805 can be configured to control the ultraviolet radiation sources 30 to direct ultraviolet radiation towards the internal walls of a fluid transport conduit 810 as described herein. The sensors 64 are configured to acquire data processed by the computer system 820 to monitor a set of attributes regarding the cleaning treatment of the fluid transport conduit 810 over a period of time. As illustrated, the sensors 64 can acquire data used by the computer system 820 to monitor the set of attributes (e.g., operating parameters, ultraviolet radiation characteristics).

It is understood that the set of attributes for the fluid transport conduit 810 can include any combination of one or more of: a frequency of the usage of the fluid transport conduit 810, a presence of contaminants and biological activity on a surface of the fluid transport conduit 810, a usage of the fluid transport conduit 810, a disinfection schedule history for the fluid transport conduit 810, and/or the like.

In the case of determining a presence of biological activity on the fluid transport conduit 810, a sensor 64 can also determine a location of the biological activity, a type of biological activity (e.g., type of organism), a concentration of the biological activity, an estimated amount of time an organism has been in a growth phase (e.g., exponential growth and/or stationary), and/or the like. Furthermore, a sensor 64 can determine information on the variation of the contaminant and biological activity over time, such as a growth rate, a rate with which an area including the contaminant and biological activity is spreading, and/or the like. In an embodiment, a set of contaminant and biological activity dynamics are related to various attributes of contaminants, bacteria and/or virus activity present on the interior walls of the fluid transport conduit 810, including, for example, the presence of detectable contaminant, bacteria and/or virus activity, measured contaminant, bacteria and/or virus population/concentration time dynamics, growth phase, and/or the like.

The computer system 820 can be configured to control and adjust a direction, an intensity, a pattern, and/or a spectral power (e.g., wavelength) of the set of ultraviolet radiation sources 30, based on data received from the sensors 64. The computer system 820 can control and adjust each property of the set of ultraviolet radiation sources 30 independently. For example, the computer system 820 can adjust the intensity, time duration, and/or time scheduling (e.g., including duration (e.g., exposure/illumination time)), duty cycle, time between exposures/illuminations, and/or the like) of the ultraviolet radiation sources 30 for a given wavelength. Each of the properties of the ultraviolet radiation sources 30 can be adjustable and controlled by the computer system 820 according to data provided by the sensors 64.

For example, the computer system 820 can be configured to adjust the direction of the ultraviolet radiation according to a location of the contaminant and biological activity detected on the interior of the fluid transport conduit 810 using any solution. The computer system 820 can be configured to utilize a target timing, intensity, and/or spectral power of the ultraviolet radiation according to a type of contaminant and biological activity. That is, the sensors 64 can sense locations of higher levels of contaminant and biological activity on the surface of the fluid transport conduit 810, and the ultraviolet radiation sources 30 can be configured by the computer system 820 to direct higher doses (by increasing intensity or exposure) of ultraviolet radiation at the locations with higher levels of contaminant and biological activity (e.g., non-uniform ultraviolet radiation).

In one embodiment, the computer system 820 can be configured to set a periodic or an aperiodic schedule for the ultraviolet radiation to be delivered to the fluid transport conduit 810. This (periodic or aperiodic) schedule can be interrupted when a sensor determines the walls of the fluid transport conduit 810 do not have any presence of contaminant and biological activity. In this manner, the computer system 820 can be configured to turn off the ultraviolet radiation.

One of the sensors 64 can include a radiation detector for detecting an amount of radiation to which a surface is exposed during a cleaning treatment. The radiation can include any type of radiation, including, for example, ultraviolet, visible, infrared, microwave, and/or the like. The amount of radiation to which the surface is exposed can be used by the computer system 820 to determine if any additional radiation is required for disinfection.

It is understood that the environment 900 may include the power source 845 to supply power to one or more of the various components depicted in FIG. 16, such as the ultraviolet radiation sources 30, the sensors 64, the control unit 805, and/or the like.

The foregoing description of various aspects of the invention has been presented for purposes of illustration and description. It is not intended to be exhaustive or to limit the invention to the precise form disclosed, and obviously, many modifications and variations are possible. Such modifications and variations that may be apparent to an individual in the art are included within the scope of the invention as defined by the accompanying claims.

What is claimed is:

1. A fluid transport conduit treatment system, comprising:
  a fluid transport conduit having an inner surface and an outer surface, wherein the fluid transport conduit includes a plurality of ultraviolet transparent windows distributed on the outer surface of the conduit and ultraviolet reflective material on the inner surface of the conduit;
  a light guiding layer enclosing the fluid transport conduit;
  a plurality of ultraviolet radiation sources coupled to the light guiding layer, wherein each of the ultraviolet radiation sources is configured to emit ultraviolet radiation through at least one of the ultraviolet transparent windows, wherein the light guiding layer is configured to receive the ultraviolet radiation and guide the ultraviolet radiation into an internal portion of the fluid transport conduit towards the ultraviolet reflective material, wherein the ultraviolet reflective material is configured to recycle the ultraviolet radiation throughout the internal portion of the fluid transport conduit, the recycled ultraviolet radiation contacting internal walls on the inner surface of the fluid transport conduit and
  a control unit to direct the plurality of ultraviolet radiation sources to deliver a predetermined dosage of ultraviolet radiation to the internal walls of the fluid transport conduit for a predetermined duration.

2. The fluid transport conduit treatment system of claim 1, wherein the light guiding layer comprises a plurality of ports, each port separating segments of the light guiding layer, and wherein each port is configured to receive one of the plurality of ultraviolet radiation sources.

3. The fluid transport conduit treatment system of claim 2, further comprising a plurality of reflective elements configured for placement over the plurality of ports, wherein each port without an ultraviolet radiation source coupled thereto has one of the plurality of reflective elements placed there over, and each port having an ultraviolet radiation source coupled thereto has one of the plurality of reflective elements placed over both the ultraviolet radiation source and the port.

4. The fluid transport conduit treatment system of claim 1, wherein the fluid transport conduit comprises a set of ultraviolet transparent domains on the inner surface of the conduit, each ultraviolet transparent domain located adjacent one of the ultraviolet transparent windows, wherein each ultraviolet transparent domain is configured for ultraviolet transmission and light guiding of ultraviolet radiation into the internal portion of the fluid transport conduit.

5. The system of claim 4, wherein the ultraviolet reflective material comprises segments of ultraviolet reflective elements, wherein each segment of ultraviolet reflective material is placed between ultraviolet transparent domains.

6. The system of claim 5, wherein at least one of the segments of ultraviolet reflective elements comprises a porous section having a multitude of pores.

7. The system of claim 6, further comprising a cleansing fluid source operatively coupled to the fluid transport conduit, the light guiding layer, and the control unit, wherein the cleansing fluid source is configured to deliver a cleaning fluid into the internal portion of the fluid transport conduit through the light guiding layer and each of the segments of ultraviolet reflective elements having the porous section with the multitude of pores, the cleansing fluid dislodging contaminants from the internal walls consequent to passing through the porous section.

8. The fluid transport conduit treatment system of claim 1, wherein the plurality of ultraviolet radiation sources are distributed over the surface area of the fluid transport conduit.

9. The fluid transport conduit treatment system of claim 1, wherein the plurality of ultraviolet radiation sources cover only a limited portion of surface area of the fluid transport conduit, wherein the plurality of ultraviolet radiation sources extend uniformly in an axial direction from a first end of the fluid transport conduit to an opposing second end of the fluid transport conduit.

10. The system of claim 1, wherein the ultraviolet reflective material comprises a diffusive ultraviolet reflective layer disposed on the inner surface of the fluid transport conduit in a location that opposes a direction that ultraviolet radiation emitted from the plurality of ultraviolet radiation sources enters into the internal portion of the conduit.

11. A system, comprising:
a fluid transport conduit having an inner surface with ultraviolet reflective material;
a plurality of ultraviolet radiation sources configured to emit ultraviolet radiation;
a light guiding layer enclosing the fluid transport conduit, wherein the light guiding layer is configured to direct the ultraviolet radiation emitted from the plurality of ultraviolet radiation sources into the fluid transport conduit to irradiate internal walls on the inner surface of the fluid transport conduit, wherein the light guiding layer is configured to receive the ultraviolet radiation and guide the ultraviolet radiation into an internal portion of the fluid transport conduit towards the ultraviolet reflective material, wherein the ultraviolet reflective material is configured to recycle the ultraviolet radiation throughout the internal portion of the conduit, the recycled ultraviolet radiation contacting the internal walls on the inner surface of the fluid transport conduit;
a control unit to direct the plurality of ultraviolet radiation sources to emit a predetermined dosage of ultraviolet radiation to the internal walls on the inner surface of the fluid transport conduit via the light guiding layer for a predetermined duration; and
a power source to provide power to the plurality of ultraviolet radiation sources and the control unit.

12. The system of claim 11, further comprising a cleansing mixing unit located within the fluid transport conduit, wherein the cleansing mixing unit is configured to mix a chemical de-scaler with fluid in the fluid transport conduit, the mixing of the chemical de-scaler with the fluid promoting dislodgment of contaminants from the internal walls on the inner surface of the fluid transport conduit.

13. The system of claim 11, wherein the plurality of ultraviolet radiation sources, the light guiding layer, the control unit, and the power source form a disinfection module adapted for connection to additional sections of the fluid transport conduit, wherein the disinfection module forms a cross-connection between two adjacent sections of the fluid transport conduit.

14. The system of claim 11, further comprising at least one sensor to sense an intensity of a distribution of ultraviolet radiation within the light guiding layer.

15. The system of claim 11, wherein at least a portion of the internal walls on the inner surface of the fluid transport conduit comprises one of a non-biofouling material and an ultraviolet photo-catalyst.

16. A system, comprising:
a fluid transport conduit having an inner surface with ultraviolet reflective material and ultraviolet transparent sections placed between the ultraviolet reflective material;
a light guiding layer enclosing the fluid transport conduit, wherein the light guiding layer comprises segments of ultraviolet reflective elements and an ultraviolet extraction surface to diffusively scatter ultraviolet radiation from the light guiding layer,
a plurality of ultraviolet radiation sources operatively coupled to the light guiding layer to direct ultraviolet radiation into an internal portion of the fluid transport conduit, wherein the light guiding layer receives the ultraviolet radiation emitted from the plurality of ultraviolet radiation sources and guides the ultraviolet radiation through the ultraviolet transparent sections on the inner surface of the fluid transport conduit via the segments of ultraviolet reflective elements and the ultraviolet extraction surface, the emitted ultraviolet radiation penetrating into the internal portion of the fluid transport conduit, wherein the ultraviolet reflective material on the inner surface the fluid transport conduit recycles the ultraviolet radiation within the internal portion of the conduit, the recycled ultraviolet radiation contacting internal walls on the inner surface of the fluid transport conduit; and
a control unit to adjust a plurality of operating parameters of the plurality of ultraviolet radiation sources as a function of removal of contaminants from the internal walls of the fluid transport conduit, wherein the plurality of operating parameters include a duration that the ultraviolet radiation sources emit ultraviolet radiation, a dosage of ultraviolet radiation delivered by the ultraviolet radiation sources, and a power setting for operating the ultraviolet radiation sources.

17. The system of claim 16, further comprising at least one sensor to monitor one of the operating parameters during disinfection of the internal walls of the fluid transport conduit with the ultraviolet radiation, the control unit controlling the disinfecting of the internal walls of the fluid transport conduit as a function of the monitoring by the sensor.

18. The system of claim 16, wherein the fluid transport conduit comprises a porous section extending from an outer surface of the fluid transport conduit to the internal walls of the fluid transport conduit.

19. The system of claim 18, further comprising a cleansing fluid source, and wherein the light guiding layer comprises a fluid intake port that is configured to deliver a cleansing fluid from the cleansing fluid source to the porous section of the fluid transport conduit to clean the internal walls of the fluid transport conduit.

20. The system of claim 16, wherein the ultraviolet transparent sections of the fluid transport conduit form rigid domains of conduit, and sections of the fluid transport conduit without the ultraviolet transparent sections form flexible domains of conduit.

\* \* \* \* \*